(12) United States Patent
Wood et al.

(10) Patent No.: US 6,451,887 B1
(45) Date of Patent: Sep. 17, 2002

(54) BENZOTRIAZOLES CONTAINING α-CUMYL GROUPS SUBSTITUTED BY HETEROATOMS AND COMPOSITIONS STABILIZED THEREWITH

(75) Inventors: Mervin G. Wood, Poughquag; Joseph Suhadolnik, Yorktown Heights; Ramanathan Ravichandran, Montebello; Jacqueline Lau, Jericho; Carmen Hendricks-Guy, White Plains, all of NY (US); Christophe Bulliard, Basel (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/632,216

(22) Filed: Aug. 3, 2000

(51) Int. Cl.⁷ .................... C08K 5/3475; C07D 249/20
(52) U.S. Cl. .................. 524/91; 548/259; 548/260; 548/261
(58) Field of Search ............... 548/259, 260, 548/261; 524/91; 514/359; 424/59; 568/333

(56) References Cited

U.S. PATENT DOCUMENTS

| | | | | |
|---|---|---|---|---|
| 3,004,896 A | * | 10/1961 | Heller et al. ............... 524/91 |
| 3,387,035 A | * | 6/1968 | Gray et al. ............... 568/333 |
| 3,823,112 A | * | 7/1974 | Ponder ................... 524/91 |
| 4,127,586 A | * | 11/1978 | Rody et al. ............... 548/259 |
| 4,278,589 A | * | 7/1981 | Dexter et al. ............. 548/259 |
| 4,727,158 A | | 2/1988 | Seltzer et al. ............. 548/260 |
| 4,760,148 A | * | 7/1988 | Seltzer et al. ............. 548/260 |
| 4,904,712 A | | 2/1990 | Seltzer et al. ............. 524/91 |
| 4,999,433 A | * | 3/1991 | Prestel et al. ............. 548/260 |
| 5,097,041 A | | 3/1992 | Higel et al. ............... 548/260 |
| 5,124,723 A | | 6/1992 | Laver .................... 346/1.1 |
| 5,142,059 A | * | 8/1992 | Burdeska et al. .......... 548/260 |
| 5,181,935 A | | 1/1993 | Reinert et al. ............. 8/442 |
| 5,274,015 A | * | 12/1993 | Deslauriers et al. ........ 548/260 |
| 5,292,890 A | | 3/1994 | Moshchitsky et al. ...... 548/260 |
| 5,312,852 A | * | 5/1994 | Falk et al. ................ 548/261 |
| 5,574,166 A | * | 11/1996 | Winter et al. ............. 548/260 |
| 5,716,667 A | * | 2/1998 | Kashiwada et al. ......... 524/99 |
| 5,932,142 A | * | 8/1999 | Yamauchi et al. .......... 548/259 |
| 5,977,219 A | | 11/1999 | Ravichandran et al. ...... 524/91 |
| 6,166,218 A | * | 12/2000 | Ravichandran et al. ..... 548/260 |
| 6,187,845 B1 | * | 2/2001 | Renz et al. ............... 524/91 |

FOREIGN PATENT DOCUMENTS

| | | |
|---|---|---|
| EP | 0738718 A1 | 10/1996 |
| WO | 98/41186 | 9/1998 |
| WO | 00/66676 | 4/2000 |

OTHER PUBLICATIONS

Jozef Luston "Physical Loss of Stabilizers From Polymers"—Developments in Polymer Stabilization=2, 185–240, ed. Gerald Scott Applied Science Publishers, Ltd. 1980.*

* cited by examiner

Primary Examiner—Veronica P. Hoke
(74) Attorney, Agent, or Firm—Tyler A. Stevenson; Luther A. R. Hall

(57) ABSTRACT

2H-Benzotriazole UV absorbers substituted at the 3-position and/or the 5-position of the phenyl ring by α-cumyl moiety which is substituted by a heteroatom are particularly photostable in automotive coatings, and are of low color and exhibit low volatility in thermoplastic compositions.

40 Claims, No Drawings

BENZOTRIAZOLES CONTAINING α-CUMYL GROUPS SUBSTITUTED BY HETEROATOMS AND COMPOSITIONS STABILIZED THEREWITH

The instant invention pertains to 2H-benzotriazole UV absorbers substituted at the 3-position and/or the 5-position of the phenyl ring by α-cumyl moiety which is substituted by a group containing a heteroatom.

BACKGROUND OF THE INVENTION

One of the most important classes of UV absorbers are the 2H-benzotriazoles. There are a myriad of patents and other references to these materials and their compositions. Indeed, several of the 2H-benzotriazole UV absorbers have achieved great commercial importance for a host of end-use applications. Several of these commerical compounds are substituted by one or more unsubstituted α-cumyl moieties.

Benzotriazole UV absorbers which are substituted at the 5-position of the benzo ring by an electron withdrawing group exhibit enhanced durability and very low loss rates when incorporated into automotive coatings. This is particularly the case when the 3-position of the phenyl ring is also substituted by phenyl or phenylalkyl such as α-cumyl. Compounds where the 5-position of the benzo ring are substituted by perfluoroalkyl such as trifluoromethyl are particularly of interest for both their enhanced durability and for their excellent solubility and excellent color properties in some thermoplastic compositions when the phenyl ring is substituted at the 3-position by hydrogen or tert-alkyl.

It is well known that the stabilization and other physical properties exhibited by the 2H-benzotriazole UV absorbers can be markedly altered depending on the nature and location of the various substituents used to modify the basic 2H-benzotriazole structure.

Although there has been some generic disclosure of substituted α-cumyl groups on benzotriazoles, none of these compounds have ever been exemplified nor prepared and their properities evaluated.

U.S. Pat. Nos. 4,727,158 and 4,904,712 describe 2H-benzotriazole compounds which are substituted at the 5-position on the benzo ring by higher alkyl groups of 8 to 18 carbon atoms. While it is generically disclosed that these compounds could be substituted on the 3- and/or 5-positions of the phenyl ring by α-cumyl or α-cumyl substituted by alkyl of 1 to 4 carbon atoms or by halogen, none of such compounds were actually prepared nor tested.

U.S. Pat. No. 5,097,041 teaches that benzotriazole UV absorbers can be substituted on the 5-position of the phenyl ring by phenyl substituted by chloro, but this patent does not teach α-cumyl substituted by chloro at any point in the benzotriazole molecule.

WO 98/41186 is directed to hair dye compositions and the various components which may be included therein. This reference contains a host of generic structures for such components including 2H-benzotriazoles. This reference in that regards is similar to U.S. Pat. Nos. 4,727,158 and 4,904,712 and does not exemplify nor describe specifically any benzotriazole substituted by an α-cumyl group itself substituted by a heteroatom.

U.S. Pat. No. 5,097,041 describes the purification of benzotriazoles where the group at the 5-position of the phenyl ring can be phenyl substituted by chloro.

DETAILED DISCLOSURE

The instant invention pertains to novel benzotriazole UV absorbers having enhanced stability and durability and a low loss rate when incorporated into automotive coatings. These new benzotriazole UV absorbers are also soluble in a variety of substrates including thermoplastic polymers and often are essentially colorless even though absorbing in the 350–390 nm range.

More specifically, the instant invention pertains to new benzotriazole compounds of formula I, II or III:

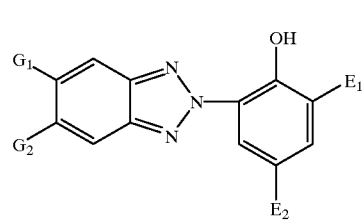

(I)

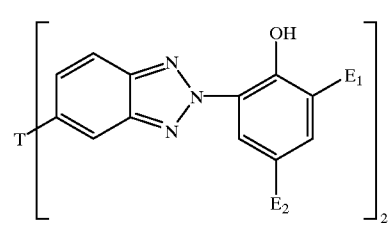

(II)

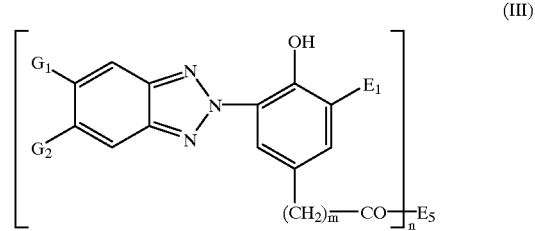

(III)

wherein $G_1$ is hydrogen or halogen, $G_2$ is hydrogen, cyano, perfluoroalkyl of 1 to 12 carbon atoms, halogen, —CO—$G_3$, —COO$G_3$, —CONH$G_3$, —CON($G_3$)$_2$, $E_3$SO—, $E_3$SO$_2$—, nitro, —P(O)(C$_6$H$_5$)$_2$, —P(O)(O$G_3$)$_2$,

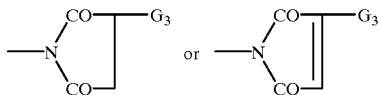

$G_3$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms, $E_1$ is hydrogen, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or $E_1$ is alkyl of 1 to 24 carbon atoms substituted by one or two hydroxy groups;

or $E_1$ is alkyl of 1 to 24 carbon atoms, alkenyl of 2 to 18 carbon atoms, said alkyl or said alkenyl substituted by one or more —OCOE$_{11}$, —OE$_4$, —NCO, —NHCOE$_{11}$, or —NE$_7$E$_8$, or mixtures thereof, where E$_4$ is straight or branched chain alkyl of 1 to 24 carbon atoms or straight or branched chain alkenyl of 2 to 18 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$, or mixtures thereof, or E$_1$ is a group of formula IV or V:

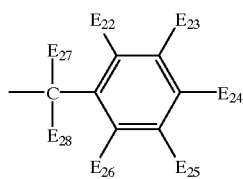

(IV)

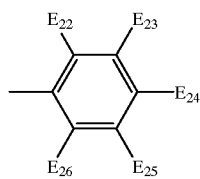

(V)

where

E$_{27}$ and E$_{28}$ are independently alkyl of 1 to 18 carbon atoms, or cycloalkyl of 5 to 12 carbon atoms;

E$_{22}$, E$_{23}$, E$_{24}$, E25 and E26 are independently hydrogen, halogen, straight or branched alkyl of 1 to 18 carbon atoms, alkenyl of 2 to 18 carbon atoms, said alkyl or said alkenyl substituted by one or more halogen, —OCOE$_{11}$, —OE$_4$, —NCO, —NHCOE$_{11}$ or —NE$_7$E$_8$, or mixtures thereof, where E$_4$ is straight or branched chain alkyl of 1 to 24 carbon atoms or straight or branched chain alkenyl of 2 to 18 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$, or mixtures thereof; or E$_{22}$, E$_{23}$, E$_{24}$, E$_{25}$ and E$_{26}$ are independently phenyl, —OH, —OCOE$_{11}$, —OE$_{29}$, —NCO, —NHCOE$_{11}$ or —NE$_7$E$_8$, cyano, nitro, perfluoroalkyl of 1 to 12 carbon atoms, —COG$_3$, —COOG$_3$, —CON(G$_3$)$_2$, —CONHG$_3$, E$_3$S—, E$_3$SO—, E$_3$SO$_2$—, —P(O)(C$_6$H$_5$)$_2$, —P(O))OG$_3$)$_2$, —SO$_2$—X$_1$—E$_{29}$;

X$_1$ is —O—, —NH— or —NE$_4$—;

E$_{29}$ is straight or branched chain alkyl of 1 to 24 carbon atoms, straight or branched chain alkenyl of 2 to 18 carbon atoms, said alkyl or said alkenyl substituted by one or more —OH, —OCOE$_{11}$, —OE$_4$, —NCO, —NHCOE$_{11}$, —NE$_7$E$_8$, phthalimido,

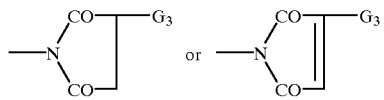

or mixtures thereof, where E$_4$ is straight or branched chain alkyl of 1 to 24 carbon atoms or alkenyl of 2 to 18 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$, or mixtures thereof; or E$_{29}$ is phenyl or phenylalkyl of 7 to 15 carbon atoms, or said phenyl or said phenylalkyl substituted by one to three alkyl groups of 1 to 4 carbon atoms;

E$_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or E$_2$ is alkyl of 1 to 24 carbon atoms or said alkenyl of 2 to 18 carbon atoms substituted by one or more —OH, —OCOE$_{11}$, —OE$_4$, —NCO, —NHCOE$_{11}$ or —NE$_7$E$_8$, or mixtures thereof, where E$_4$ is straight or branched chain alkyl of 1 to 24 carbon atoms or aLkenyl of 2 to 18 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$ groups or mixtures thereof, or E$_2$ is a group of formula IV or formula V as described above;

n is 1 or 2, when n is 1, E$_5$ is OE$_6$ or NE$_7$E$_8$, or

E$_5$ is —PO(OE$_{12}$)$_2$, —OSi(E$_{11}$)$_3$ or —OCO—E$_{11}$, or straight or branched chain C$_1$–C$_{24}$alkyl which is interrupted by —O—, —S—or —NE$_{11}$ and which can be unsubstituted or substituted by —OH or —OCO—E$_{11}$, C$_5$–C$_{12}$ cycloalkyl which is unsubstituted or substituted by —OH, straight chain or branched C$_2$–C$_{18}$alkenyl which is unsubstituted or substituted by —OH, C$_7$–C$_{15}$aralkyl, —CH$_2$—CHOH—E$_{13}$ or glycidyl, E$_6$ is hydrogen, straight or branched chain C$_1$–C$_{24}$alkyl which is unsubstituted or substituted by one or more OH, OE$_4$ or NH$_2$ groups, or —OE$_6$ is —(OCH$_2$CH$_2$)$_w$OH or —(OCH$_2$CH$_2$)$_w$OE$_{21}$ where w is 1 to 12 and E$_{21}$ is alkyl of 1 to 12 carbon atoms, E$_7$ and E$_8$ are independently hydrogen, alkyl of 1 to 18 carbon atoms, straight or branched chain C$_3$–C$_{18}$alkyl which is interrupted by —O—, —S— or —NE$_{11}$—, straight or branched chain alkenyl of 2 to 18 carbon atoms, C$_5$–C$_{12}$cycloalkyl, C$_6$–C$_{14}$aryl or C$_1$–C$_3$hydroxylalkyl, or E$_7$ and E$_8$ together with the N atom are a pyrrolidine, piperidine, piperazine or morpholine ring, or E$_5$ is —X—(Z)$_p$—Y—E$_{15}$ wherein X is —O— or —N(E$_{16}$)—, Y is —O— or —N(E$_{17}$)—, Z is C$_2$–C$_{12}$-alkylene, C$_4$–C$_{12}$-alkylene interrupted by one to three nitrogen atoms, oxygen atoms or a mixture thereof, or is C$_3$–C$_{12}$-alkylene, butenylene, butynylene, cyclohexylene or phenylene, each substituted by a hydroxyl group, m is zero, 1 or 2, p is 1, or p is also zero when X and Y are —N(E$_{16}$)— and —N(E$_{17}$)—, respectively, E$_{15}$ is a group —CO—C(E$_{18}$)=C(H)E$_{19}$ or, when Y is —N(E$_{17}$)—, forms together with E$_{17}$ a group —CO—CH=CH—CO—, wherein E$_{18}$ is hydrogen or methyl, and E$_{19}$ is hydrogen, methyl or —CO—X—E$_{20}$, wherein E$_{20}$ is hydrogen, C$_1$–C$_{12}$-alkyl or a group of the formula:

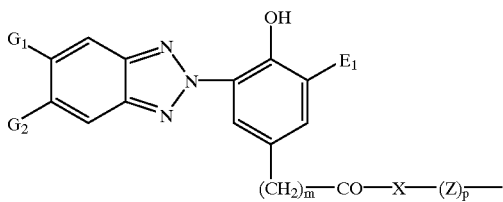

wherein the symbols $E_1$, $G_2$, X, Z, m and p have the meanings defined above, and $E_{16}$ and $E_{17}$ independently of one another are hydrogen, $C_1$–$C_{12}$-alkyl, $C_3$–$C_{12}$-alkyl interrupted by 1 to 3 oxygen atoms, or is cyclohexyl or $C_7$–$C_{15}$aralkyl, and $E_{16}$ together with $E_{17}$ in the case where Z is ethylene, also forms ethylene, when n is 2, $E_5$ is one of divalent radicals —O—, $E_9$—O— or —N($E_{11}$)—$E_{10}$—N($E_{11}$)—, $E_9$ is $C_2$–$C_8$alkylene, $C_4$–$C_8$alkenylene, $C_4$alkynylene, cyclohexylene, straight or branched chain $C_4$–$C_{10}$alkylene which is interrupted by —O— or by —CH$_2$—CHOH—CH$_2$—O—$E_{14}$—O—CH$_2$—CHOH—CH$_2$—, $E_{10}$ being straight or branched chain $C_2$–$C_{12}$alkylene which may be interrupted by —O—, cyclohexylene, or

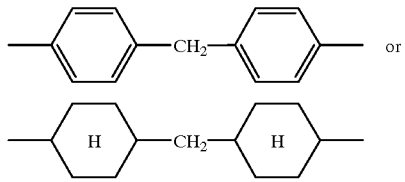

or $E_{10}$ and $E_{11}$ with the two nitrogen atoms form a piperazine ring, $E_{14}$ is straight or branched chain $C_2$–$C_8$alkylene, straight or branched chain $C_4$–$C_{10}$alkylene which is interrupted by —O—, cycloalkylene, arylene or

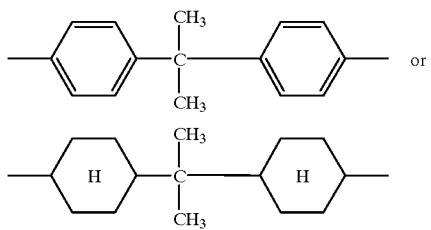

$E_{11}$ is hydrogen, straight or branched chain $C_1$–$C_{18}$alkyl, $C_5$–$C_{12}$cycloalkyl, straight or branched chain $C_2$–$C_{18}$alkenyl, $C_6$–$C_{14}$aryl or $C_7$–$C_{15}$aralkyl, $E_{12}$ is straight or branched chain $C_1$–$C_{18}$alkyl, straight or branched chain $C_3$–$C_{18}$alkenyl, $C_5$–$C_{10}$cycloalkyl, $C_6$–$C_{16}$aryl or $C_7$–$C_{15}$aralkyl, $E_{13}$ is hydrogen, straight chain or branched $C_1$–$C_{18}$alkyl which is substituted by —PO(O$E_{12}$)$_2$, phenyl which is unsubstituted or substituted by OH, $C_7$–$C_{15}$aralkyl or —CH$_2$O$E_{12}$, $E_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, T is —SO—, —SO$_2$—, —SO—E—SO—, —SO$_2$—E—SO$_2$—, —CO—, —CO—CO—, —CO—CH$_2$—CO—, —CO—E—CO—, —COO—E—OCO— or —CO—NG$_5$—E—NG$_5$—CO—, where E is alkylene of 2 to 12 carbon atoms, cycloalkylene of 5 to 12 carbon atoms, or alkylene interrupted or terminated by cyclohexylene of 8 to 12 carbon atoms;

$G_5$ is $G_3$ or hydrogen, and with the proviso that at least one of $E_1$ and $E_2$ must contain a group of formula IV or formula V; and with the further proviso that when $E_{22}$ to $E_{26}$ all together contain 2 to 4 hydrogen atoms, the remaining $E_{22}$ to $E_{26}$ groups are not alkyl of 1 to 4 carbon atoms; or that $E_{22}$ to $E_{26}$ cannot each be hydrogen.

Preferably, the new benzotriazole is a compound of formula I:

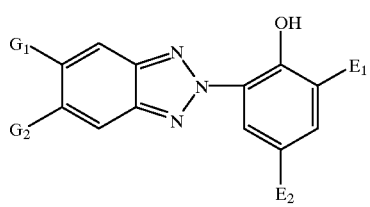

(I)

wherein $G_1$ is hydrogen, $G_2$ is hydrogen, cyano, CF$_3$—, fluoro, chloro, —CO—$G_3$, —COO$G_3$ or $E_3$SO$_2$—, $G_3$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms, $E_1$ is a group of formula IV or formula V wherein $E_{22}$–$E_{26}$ are independently hydrogen, alkyl of 1 to 12 carbon atoms, straight or branched chain alkenyl of 2 to 18 carbon atoms, OH, cyano, —O$E_{29}$, chloro, fluoro, —OCO$E_{11}$, CF$_3$, —COO$G_3$, $E_3$S—, $E_3$SO$_2$— or —SO$_2$—NH—$E_{29}$;

$E_{27}$ and $E_{28}$ are methyl;

$E_2$ is straight or branched alkyl chain of 1 to 24 carbon atoms, straight or branched. chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or $E_2$ is said alkyl of 1 to 24 carbon atoms or straight or branched alkenyl of 2 to 18 carbon atoms; or said alkyl or said alkenyl substituted by one or more —OH, —OCO$E_{11}$, —O$E_4$, —NCO, —NHCO$E_{11}$ or —N$E_7E_8$, or mixtures thereof, where $E_4$ is straight or branched chain alkyl of 1 to 24 carbon atoms or straight or branched chain alkenyl of 2 to 18 carbon atoms; or said alkyl or said alkenyl interrupted by one or more —O—, —NH— or —N$E_4$— groups or mixtures thereof and which can be unsubstituted or substituted by one or more —OH, —O$E_4$ or —NH$_2$ groups or mixtures thereof; or $E_2$ is a group of formula IV or formula V wherein $E_{22}$–$E_{26}$ are independently hydrogen, alkyl of 1 to 12 carbon atoms, straight or branched chain alkenyl of 2 to 18 carbon atoms, OH, cyano, —OE$_{29}$, chloro, fluoro, —OCOE$_{11}$, CF$_3$, —COOG$_3$, E$_3$S—, E$_3$SO$_2$— or —SO$_2$—NH—E$_{29}$;

E$_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms; and where E$_{11}$ and E$_{29}$ are as defined above.

Most preferably, the instant compounds of formula I is a. 5-trifluoromethyl-2-[2-hydroxy-3-(4-methoxy-α-cumyl)-5-tert-butylphenyl]-2H-benzotriazole;
b. 5-trifluoromethyl-2-[2-hydroxy-3-(4-fluoro-α-cumyl)-5-tert-octylphenyl]-2H-benzotriazole;
c. 2-[2-hydroxy-3-(4-methoxy-α-cumyl)-5-tert-butylphenyl]-2H-benzotriazole;
d. 2-[2-hydroxy-3-(4-chloro-α-cumyl)-5-tert-butylphenyl]-2H-benzotriazole;
e. 5-chloro-2-[2-hydroxy-3-(4-chloro-α-cumyl)-5-tert-butylphenyl]-2H-benzotriazole;
f. 5-chloro-2-[2-hydroxy-3,5-di-(4-chloro-α-cumyl)phenyl]-2H-benzotriazole;
g. 5-chloro-2-[2-hydroxy-3,5-di-(4-methoxy-α-cumyl)phenyl]-2H-benzotriazole;
h. 5-trifluoromethyl-2-[2-hydroxy-3-(4-chloro-α-cumyl)-5-tert-butylphenyl]-2H-benzotriazole;
i. 5-chloro-2-[2-hydroxy-3-(4-methoxy-α-cumyl)-5-tert-butylphenyl]-2H-benzotriazole;
j. 2-{(2-hydroxy-3-[4-(2-dimethylaminoethyl)aminosulfonyl-α-cumyl]-5-tert-octylphenyl}-2H-benzotriazole;
k. 2{2-hydroxy-3-[4-(3-dimethylaminopropyl)aminosulfonyl-α-cumyl]-5-tert-octylphenyl}-2H-benzotriazole;
l. 5-carboxy-2-[2-hydroxy-3-(4-chloro-α-cumyl)-5-tert-butylphenyl]-2H-benzotriazole;
m. 5-methoxycarbonyl-2-[2-hydroxy-3-(4-chloro-α-cumyl)-5-tert-butylphenyl]-2H-benzotriazole;
n. 2-{2-hydroxy-3-[4-(2-hydroxyethoxy)-α-cumyl]-5-tert-butylphenyl}-2H-benzotriazole;
o. 2-{2-hydroxy-3-[4-(2-phthalimidoethoxy)-α-cumyl]-5-tert-butylphenyl}-2H-benzotriazole;
p. 5-trifluoromethyl-2-[2-hydroxy-3-(3-isopropenyl-α-cumyl)-5-tert-octylphenyl]-2H-benzotriazole;
q. 5-trifluoromethyl-2-{2-hydroxy-3-[3-(2-hydroxy-1-methylethyl)-α-cumyl]-5-tert-octylphenyl}-2H-benzotriazole;
r. 5-trifluoromethyl-2-{2-hydroxy-3-[3-(2-methacryloyloxy-1-methylethyl)-α-cumyl]-5-tert-octylphenyl}-2H-benzotriazole;
s. 5-chloro-2-[2-hydroxy-3-(4-carboxy-α-cumyl)-5-methylphenyl]-2H-benzotriazole;
t. 5-chloro-2-[2-hydroxy-3-(4-octadecyloxycarbonyl-α-cumyl)-5-methylphenyl]-2H-benzotriazole; or
u. 2-[2-hydroxy-3-(4-octadecylaminosulfonyl-α-cumyl)-5-tert-octylphenyl]-2H-benzotriazole.

The instant invention also pertains to a composition stabilized which comprises (a) an organic material subject to degradation by heat, light or oxygen, and
(b) an effective stabilizing amount of a compound of formula I, II or III as described above.

Preferably, the organic material is a natural, semi-synthetic or synthetic polymer, especially a thermoplastic polymer.

Most preferably, the polymer is a polyolefin or polycarbonate, especially polyethylene or polypropylene; most especially polypropylene; or the polymer is a styrenic, ABS, a nylon, a polyester such as poly(ethylene terephthalate) or poly(butylene terephthalate), a polyurethane, an acrylate, a rubber modified styrenic, poly(vinyl chloride), poly(vinyl butyral), polyacetal (polyoxymethylene), poly(ethylene naphthalene-dicarboxylate), or other blends or copolymers such as poly (ethylene/1,4-cyclohexylene-dimethylene-terephthalate) PETG or an ionomer as described on page 29.

In another preferred embodiment of the instant invention, the organic material is a resin selected from the group consisting of a thermoset acrylic melamine resin, an acrylic. urethane resin, an epoxy carboxy resin, a silane modified acrylic melamine, an acrylic resin with carbamate pendant groups crosslinked with melamine or an acrylic polyol resin crosslinked with melamine containing carbamate groups.

Most preferably, the resin is a thermoset acrylic melamine resin or an acrylic urethane resin.

In yet another preferred embodiment of the instant invention, the organic material is a recording material.

The recording materials according to the invention are suitable for pressure-sensitive copying systems, photocopying systems using microcapsules, heat-sensitive copying systems, photographic materials and ink jet printing.

The recording materials according to the invention are distinguished by an unexpected improvement in quality, especially with regard to the fastness to light.

The recording materials according to the invention have the construction known for the particular use. They consist of a customary carrier, for example, paper or plastic film, which has been coated with one or more layers. Depending on the type of material, these layers contain the appropriate necessary components, in the case of photographic materials, for example, silver halide emulsions, dye couplers, dyes and the like. Material particularly suitable for ink jet printing has a layer particularly absorptive for ink on a customary carrier. Uncoated paper can also be employed for ink jet printing. In this case the paper acts at the same time as the carrier material and as the ink-absorbent layer. Suitable material for ink jet printing is, for example, described in U.S. Pat. No. 5,073,448 which is incorporated herein by reference.

The recording material can also be transparent as, for example, in the case of projection films.

The compounds of formula I, II or III can be incorporated into the carder material as early as the production of the latter, in the production of paper, for example, being added to the paper pulp. A second method of application is to spray the carder material with an aqueous solution of compounds of formula I, II or III or to add the compounds to the coating composition.

Coating compositions intended for transparent recording materials suitable for projection cannot contain any particles which scatter light, such as pigments and fillers.

The dye-binding coating composition can contain a number of other additives, for example, antioxidants, light stabilizers (including also UV absorbers which do not fall under the scope of the UV absorbers of this invention), viscosity improvers, fluorescent brighteners, biocides and/or antistatic agents.

The coating composition is usually prepared as follows: the water-soluble components, for example, the binder, are dissolved in water and stirred together; the solid components, for example, fillers and other additives already described, are dispersed in this aqueous medium; and disperison is advantageously carried out by means of devices, for example, ultrasonic systems, turbine stirrers, homogenizers, colloid mills, bead mills, sand mills, high-speed stirrers and the like. The compounds of formula I, II or III can be easily incorporated into the coating composition.

The recording material according to this invention preferably contains 1 to 5000 mg/m$^2$, in particular 50–1200 mg/m$^2$, of a compound of formula I, II or III.

As already mentioned, the recording materials according to the invention embrace a wide field. The compounds of formula I, II or III can, for example, be employed in pressure-sensitive copying systems. They can be introduced either into the paper in order to protect the microencapsulated dye precursors there from light, or into the binder of the developer layer in order to protect the dyes formed there.

Photocopying systems using light-sensitive microcapsules which are developed by means of pressure are described in U.S. Pat. Nos. 4,416,966; 4,483,912; 4,352,200; 4,535,050; 4,535,463; 4,551,407; 4,562,137 and 4,608,330; and also in EP-A 139,479; EP-A 162,664; EP-A 164,931; EP-A 237,024; EP-A 237,025 and EP-A 260,129. In all these systems, the compounds can be put into the dye-receiving layer. The compounds can, however, also be put into the donor layer in order to protect the color formers from light.

Photographic materials which can be stabilized are photographic dyes and layers containing such dyes or precursors thereof, for example, photographic paper and films. Suitable materials are, for example, described in U.S. Pat. No. 5,364,749 which is incorporated herein by reference. The compounds of formula I, II or III act here as a UV filter against electrostatic flashes. In color photographic materials, couplers and dyes are also protected against photochemical decomposition.

The instant compounds can be used for all types of color photographic materials. For example, they can be employed for color paper, color reversal paper, direct-positive color material, color negative film, color positive film, color reversal film and the like. They are preferably used inter alia for photographic color material which contains a reversal substrate or form positives.

Color-photographic recording materials usually contain, on a support, a blue-sensitive and/or a green-sensitive and/or a red-sensitive silver halide emulsion layer and, if desired, a protection layer, with the instant compounds being, preferably, either in the green-sensitive or the red-sensitive layer or in a layer between the green-sensitive and the red-sensitive layer or in a layer on top of the silver halide emulsion layers.

The compounds of formula I, II or III can also be employed in recording materials based on the principles of photopolymerization, photoplasticization or the rupture of microcapsules, or in cases where heat-sensitive and light-sensitive diazonium salts, leuko dyes having an oxidizing agent or dye lactones having Lewis acids are used.

Furthermore, the instant compounds can be employed in recording materials for dye diffusion transfer printing, thermal wax transfer printing and non-matrix printing and for use with electrostatic, electrographic, electrophoretic, magnetographic and laser-electrophotographic printers and pen-plotters. Of the above, recording materials for dye diffusion transfer printing are preferred, for example, as described in EP-A 507,734.

The instant compounds can also be employed in inks, preferably for ink jet printing, for example, as described in U.S. Pat. No. 5,098,477 which is incorporated herein by reference.

The instant compounds also are effective in the protection of dyes present in candle wax from premature degradation and fading.

The instant compounds of formula I, II or III are also useful in adhesives used in solar films, optical films and other laminated structures against the adverse effects of ultraviolet light and actinic radiation.

The compounds of this invention exhibit superior hydrolytic stability, handling and storage stability as well as good resistance to extractability when present in a stabilized composition.

The methodology to make the instant compounds is described in the prior art. The intermediates needed to make the instant compounds are largely items of commerce.

Preferred compounds are those in which one of X and Y is —O—; and particularly those in which both X and Y are —O—.

In general polymers which can be stabilized include
1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:
  a) radical polymerisation (normally under high pressure and at elevated temperature).
  b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidenenorbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epi-chlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylo-nitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.
26. Crosslinked epoxy resins derived from polyepoxides, for example from bisglycidyl ethers or from cycloaliphatic diepoxides.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic. PUR, POM/acrylate, POM/MBS, PPO/HIPS, PPO/PA 6.6 and copolymers, PA/HDPE, PA/PP, PA/PPO.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.
31. Polysiloxanes such as the soft, hydrophilic polysiloxanes described, for example, in U.S. Pat. No. 4,259,467; and the hard polyorganosiloxanes described, for example, in U.S. Pat. No. 4,355,147.
32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
33. Radiation curable compositions containing ethylenically unsaturated monomers or oligomers and a polyunsaturated aliphatic oligomer.
34. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.05 to about 3%, and especially 0.05 to about 1%. However, some high performance films or in UV absorbing layers of laminates such as those produced by coextrusion may contain from 5–15% by weight of the instant compounds. Concentrations of 5–10% by weight are typical in certain coextrusion applications.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants
  1.1. Alkylated monophenols, for example,
    2,6-di-tert-butyl-4-methylphenol
    2-tert-butyl-4,6-dimethylphenol
    2,6-di-tert-butyl-4-ethylphenol
    2,6-di-tert-butyl-4-n-butylphenol
    2,6-di-tert-butyl-4-i-butylphenol
    2,6-di-cyclopentyl-4-methylphenol
    2-(α-methylcyclohexyl)-4,6-dimethylphenol
    2,6-di-octadecyl-4-methylphenol
    2,4,6-tri-cyclohexylphenol
    2,6-di-tert-butyl-4-methoxymethylphenol
  1.2. Alkylated hydroquinones, for example,
    2,6-di-tert-butyl-4-methoxyphenol
    2,5-di-tert-butyl-hydroquinone
    2,5-di-tert-amyl-hydroquinone
    2,6-diphenyl-4-octadecyloxyphenol
  1.3. Hydroxylated thiodiphenyl ethers, for example,
    2,2'-thio-bis-(6-tert-butyl-4-methylphenol)
    2,2'-thio-bis-(4-octylphenol)
    4,4'-thio-bis-(6-tert-butyl-3-methylphenol)
    4,4'-thio-bis-(6-tert-butyl-2-methylphenol)
  1.4. Alkylidene-bisphenols, for example,
    2,2'-methylene-bis-(6-tert-butyl-4-methylphenol)
    2,2'-methylene-bis-(6-tert-butyl-4-ethylphenol)
    2,2'-methylene-bis-[4-methyl-6-(α-methylcyclohexyl)-phenol]
    2,2'-methylene-bis-(4-methyl-6-cyclohexylphenol)
    2,2'-methylene-bis-(6-nonyl-4-methylphenol)
    2,2'-methylene-bis-[6-(α-methylbenzyl)-4-nonylphenol]
    2,2'-methylene-bis-[6-(α,α-dimethylbenzyl)-4-nonylphenol]
    2,2'-methylene-bis-(4,6-di-tert-butylphenol)
    2,2'-ethylidene-bis-(4,6-di-tert-butylphenol)
    2,2'-ethylidene-bis-(6-tert-butyl-4-isobutylphenol)
    4,4'-methylene-bis-(2,6-di-tert-butylphenol)
    4,4'-methylene-bis-(6-tert-butyl-2-methylphenol)
    1,1-bis-(5-tert-butyl-4-hydroxy-2-methylphenyl)-butane
    2,6-di-(3-tert-butyl-5-methyl-2-hydroxybenzyl)-4-methylphenol
    1,1,3-tris-(5-tert-butyl-4-hydroxy-2-methylphenyl)-butane
    1,1-bis-(5-tert-butyl-4-hydroxy-2-methylphenyl)-3-n-dodecylmercaptobutane
    ethyleneglycol bis-[3,3-bis-(3'-tert-butyl-4'-hydroxyphenyl)-butyrate]
    di-(3-tert-butyl-4-hydroxy-5-methylphenyl)-dicyclopentadiene
    di-[2-(3'-tert-butyl-2'-hydroxy-5'-methyl-benzyl)-6-tert-butyl-4-methylphenyl] terephthalate.
  1.5. Benzyl compounds, for example,
    1,3,5-tri-(3,5-di-tert-butyl-4-hydroxybenzyl)-2,4,6-trimethylbenzene
    di-(3,5-di-tert-butyl-4-hydroxybenzyl) sulfide
    3,5-di-tert-butyl-4-hydroxybenzyl-mercapto-acetic acid isooctyl ester
    bis-(4-tert-butyl-3-hydroxy-2,6-dimethylbenzyl)dithiol terephthalate
    1,3,5-tris-(3,5-di-tert-butyl-4-hydroxybenzyl) isocyanurate
    1,3,5-tris-(4-tert-butyl-3-hydroxy-2,6-dimethylbenzyl) isocyanurate
    3,5-di-tert-butyl-4-hydroxybenzyl-phosphoric acid dioctadecyl ester 3,5-di-tert-butyl-4-hydroxybenzyl-phosphoric acid monoethyl ester, calcium-salt 1.6. Acylamino-phenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.8. Esters of β-(5-tert-butyl-4-hydroxy-3-methylphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.9. Amides of β-(3-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example, diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and. 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone), bis(1-octyloxy-2,2,6,6-tetramethylpiperidin-4-yl) sebacate, 1-(2-hydroxy-2-methylpropoxy)-4-octadecanoyloxy-2,2,6,6-tetramethylpiperidine.

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis [2-hydroxy-4-(2 -hydroxy-ethoxy)phenyl]-6-(4-chlorophenyl)-s-triazine; 2,4-bis[2-hydroxy-4-(2-hydroxy-4-(2-hydroxy-ethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4,6-tri-tert-butylphenyl)-pentaerythritol diphosphite, di-(2,4-di-tert-butyl-6-methylphenyl)-pentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecyl-hydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

13. Benzofuranones and indolinones, for example those disclosed in U.S. Pat. No. 4,325,863, U.S. Pat. No. 4,338,244 or U.S. Pat. No. 5,175,312, or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-tert-butyl-3-(4-[2-hydroxyethoxy]phenyl)benzofuran-2-one],5,7-di-tert-butyl-3-(4-ethoxyphenyl)-benzofuran-2-one, 3-(4-acetoxy-3,5-dimethylphenyl)-5,7-di-tert-butyl-benzofuran-2-one, 3-(3,5-di-methyl-4-pivaloyloxyphenyl)-5,7-di-tert-butyl-benzofuran-2-one.

The co-stabilizers, with the exception of the benzofuranones listed under 13, are added for example in concentrations of 0.01 to 10%, relative to the total weight of the material to be stabilized.

Further preferred compositions comprise, in addition to components (a) and (b) further additives, in particular phenolic antioxidants, light stabilizers or processing stabilizers.

Particularly preferred additives are phenolic antioxidants (item 1 of the list), sterically hindered amines (item 2.6 of the list), phosphites and phosphonites (item 4 of the list), UV absorbers (item 2 of the list) and peroxide-destroying compounds (item 5 of the list).

Additional additives (stabilizers) which are also particularly preferred are benzofuran-2-ones, such as described, for example, in U.S. Pat. No. 4,325,863, U.S. Pat. No. 4,338,244 or U.S. Pat. No. 5,175,312.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxy-benzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl) sebacate, bis (1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2]heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis (butyl-1,2,2,6,6-pentamethyl-piperidin-4-yl)-amino-s-triazin-2-yl]-1,10-diamino-4,7-diazadecane, mixed [2,2,6,6- tetramethylpiperidin-4-yl/β,β,β'β'-tetramethyl-3,9-(2,4,8,10-tetraoxaspiro[5.5]-undecane)diethyl] 1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]-undecane)diethyl] 1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,6,6-tetramethylpiperidin-4-yln-dodecylsuccinimide, 1-acetyl3-dodecyl-7,7,9,9-tetramethyl-1,3,8-triazaspiro[4.5]decane-2,4-dione, di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], 2,4,6-tris[N-(1-cyclohexyloxy-2,2,6,6-tetramethylpiperidin-4-yl)-n-butylamino]-s-triazine, bis[8-(2-hydroxy-2-methylpropoxy)-2,2,6,6-tetramethylpiperidin-4-yl)] sebacate; a mixture of bis[1-(2-hydroxy-2-methylpropoxy)-2,2,6,6-tetramethylpiperidin-4-yl] glutarate and bis[1(2-hydroxy-2-methylpropoxy)-2,2,6,6-tetramethylpiperidin-4-yl] adipate; 1-(2-hydroxy-2-methylpropoxy)-4-octadecanoyloxy-2,2,6,6-tetramethylpiperidine; bis [1-(2-hydroxy-2-methylpropoxy)-2,2,6,6-tetramethylpiperidin-4-yl] adipate; bis[1-(2-hydroxy-2-methylpropoxy)-2,2,6,6-tetramethylpiperidin-4-yl] glutarate; bis[1-(2-hydroxy-2-methylpropoxy)-2,2,6,6-tetramethylpiperidin-4-yl] succinate; a mixture of bis[1-(2-hydroxy-2-methylpropoxy)-2,2,6,6-tetramethylpiperidin-4-yl] glutarate and bis[1-(2-hydroxy-2-methylpropoxy)-2,2,6,6-tetramethylpiperidin-4-yl] succinate; 1-(4-octadecanoyloxy-2,2,6,6-tetramethylpiperidin-1-yloxy)-2-octadecanoyloxy-2-methylpropane; 1-(2-hydroxy-2-methylpropoxy)-4-[9-(methoxy-carbonyl)nonanoyloxy]-2,2,6,6-tetramethylpiperidine; 1-(2-hydroxy-2-methylpropoxy)-4-[5-(methoxy-carbonyl)pentanoyloxy]-2,2,6,6-tetramethylpiperidine; 1-(2-hydroxy-2-methylpropoxy)-4-[3-(methoxy-carbonyl)propionyloxy]-2,2,6,6-tetramethylpiperidine; 1-(2-hydroxy-2-methylpropoxy)-4-[4-(methoxy-carbonyl)-butyryloxy]-2,2,6,6-tetramethylpiperidine; condensation product of 4-hydroxy-1-(2-hydroxy-2-methylpropoxy)-2,2,6,6-tetramethylpiperidine with hexamethylene diisocyanate and terminated with methoxy; condensation product of 4-hydroxy-1-(2-hydroxy-ethoxy)-2,2,6,6-tetramethylpiperidine with hexamethylene diisocyanate and terminated with methoxy; and the condensation product of 4-hydroxy-1-(2-hydroxy-1-phenethoxy)-2,2,6,6-tetramethylpiperidine with hexamethylene diisocyanate and terminated with methoxy.

A most preferred hindered amine compound is bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N",N"'-tetrakis[(4,6-bis(butyl-(1,2,2,6,6-pentamethylpiperidin-4-yl)amino)-s-triazine-2-yl]-1,10-diamino-4,7-diazadecane. di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], 2,4,6-tris[N-(1-cyclohexyloxy-2,2,6,6-tetramethylpiperidin-4-yl)-n-butylamino]-s-triazine, or 1-(2-hydroxy-2-methylpropoxy)-4-octadecanoyloxy-2,2,6,6-tetramethylpiperidine.

The instant composition can additionally contain another UV absorber selected from the group consisting of the benzotriazoles, the s-triazines, the oxanilides, the salicylates, the hydroxybenzophenones, the benzoates and the α-cyanoacrylates.

Particularly, the instant composition may additionally contain an effective stabilizing amount of at least one other 2-hydroxyphenyl-2H-benzotriazole; another tris-aryl-s-triazine; or hindered amine or mixtures thereof.

Preferably, the 2-hydroxyphenyl-2H-benzotriazole is selected from the group consisting of
2-(2-hydroxy-3,5-di-tert-amylphenyl)-2H-benzotriazole;
2-[2-hydroxy-3,5-di(α,α-dimethylbenzyl)phenyl]-2H-benzotriazole;
2-[2-hydroxy-3-(α,α-dimethylbenzyl)-5-tert-octylphenyl]-2H-benzotriazole;
2-{2-hydroxy-3-tert-butyl-5-[2-(omega-hydroxy-octa(ethyleneoxy)carbonyl)ethyl]phenyl}-2H-benzotriazole;
5-chloro-2-(2-hydroxy-3,5-di-tert-butylphenyl)-2H-benzotriazole;
5-chloro-2-(2-hydroxy-3-tert-butyl-5-methylphenyl)-2H-benzotriazole;
2-(2-hydroxy-5-tert-octylphenyl)-2H-benzotriazole;
2-{2-hydroxy-3-tert-butyl-5-[2-(octyloxy)carbonyl)ethyl]phenyl}-2H-benzotriazole;
(a) 5-trifluoromethyl-2-(2-hydroxy-3-α-cumyl-5-tert-octylphenyl)-2-H-benzotriazole
(b) 5-trifluoromethyl-2-(2-hydroxy -5-tert-octylphenyl)-2H-benzotriazole;
(c) 5-trifluoromethyl-2-(2-hydroxy-3,5-di-tert-octylphenyl)-2H-benzotriazole;
(d) 2,2'-methylene-bis[6-(5-trifluoromethyl-2H-benzotriazol-2-yl)-4-tert-octylphenol];
(e) methylene-2-[4-tert-octyl-6-(2H-benzotriazol-2-yl)phenol]2'-[4-tert-octyl-6-(5-2H-benzotriazol-2-yl)phenol];
(f) 3-(5-trifluoromethyl-2H-benzotriazol-2-yl)-5-tert-butyl-4-hydroxyhydrocinnamic acid;
(g) methyl 3-(5-trifluoromethyl-2H-benzotriazol-2-yl)-5-tert-butyl-4-hydroxyhydrocinnamate;
(h) isooctyl 3-(5-trifluoromethyl-2H-benzotriazol-2-yl)-5-tert-butyl4-hydroxyhydrocinnamate;
(i) 5-trifluoromethyl-2-[2-hydroxy-5-(3-hydroxypropyl)phenyl]-2H-benzotriazole;
(j) 5-trifluoromethyl-2-[2-hydroxy-5-(3-acryloyloxypropyl)phenyl]-2H-benzotriazole;
(k) 5-trifluoromethyl-2-[2-hydroxy-5-(3-methacryloyloxyethyl)phenyl]-2H-benzotriazole;
(l) 5-trifluoromethyl-2-[2-hydroxy-5-(3-acrylylaminopropyl)phenyl]-2H-benzotriazole;
(m) 5-trifluoromethyl-2-[2-hydroxy-5-(3-methacrylylaminopropyl)phenyl]-2H-benzotriazole;
(n) 5-trifluoromethyl-2-(2-hydroxy-3-α-cumyl-5-tert-butylphenyl)-2H-benzotriazole;
(o) 5-trifluoromethyl-2-(2-hydroxy-3-α-cumyl-5-nonylphenyl)-2H-benzotriazole;
(p) 5-trifluoromethyl-2-[2-hydroxy-3-α-cumyl-5-(2-hydroxyethyl)phenyl]-2H-benzotriazole;

(q) 5-trifluoromethyl-2-[2-hydroxy-3-α-cumyl-5-(3-hydroxypropyl)phenyl]-2H-benzotriazole;

(r) 5-trifluoromethyl-2-(2-hydroxy-3,5-di-tert-amylphenyl)-2H-benzotriazole;

(s) 5-trifluoromethyl-2-(2-hydroxy-3,5-di-tert-butylphenyl)-2H-benzotriazole;

(t) 5-trifluoromethyl-2-(2-hydroxy-3-dodecyl-5-methylphenyl)-2H-benzotriazole;

(u) 5-trifluoromethyl-2-[2-hydroxy-3-tert-butyl-5-(3-hydroxypropyl)phenyl]-2H-benzotriazole;

(v) 5-trifluoromethyl-2-[2-hydroxy-3tert-butyl-5-(2-hydroxyethyl)phenyl]-2H-benzotriazole;

(w) 5-trifluoromethyl-2-[2-hydroxy-5-(2-hydroxyethyl)phenyl]-2H-benzotriazole;

(x) 5-trifluoromethyl-2-(2-hydroxy-3,5-di-α-cumylphenyl)-2H-benzotriazole;

(y) 5-fluoro-2-(2-hydroxy-3,5-di-α-cumylphenyl)-2H-benzotriazole;

(z) 5-butylsulfonyl-2-(2-hydroxy-3,5-di-α-cumylphenyl)-2H-benzotriazole;

(aa) 5-butylsulfonyl-2-(2-hydroxy-3,5-di-tert-butylphenyl)-2H-benzotriazole;

(bb) 5-butylsulfonyl-2-(2-hydroxy-3,5-di-tert-octylphenyl)-2H-benzotriazole; and (cc) 5-phenylsulfonyl-2-(2-hydroxy-3,5-di-tert-butylphenyl)-2H-benzotriazole.

The instant compounds are often used in conjunction with one or more coadditive stabilizers where the coadditive stabilizer is a hindered phenolic antioxidant selected from the group consisting of neopentanetetrayl tetrakis(3,5-di-tert-butyl-4-hydroxy-hydrocinnamate, octadecyl 3,5-di-tert-butyl-4-hydroxyhydrocinnamate, 1,3,5-trimethyl-2,4,6-tris(3,5,-di-tert-butyl-4-hydroxybenzyl)benzene, 1,2-bis(3,5-di-tert-butyl-4-hydroxy-hydrocinnamoyl)hydrazine, calcium [bis(monoethyl 3,5-ditert-butyl-4-hydroxybenzyl)-phosphonate], 1,3,5-tris(3,5-di-tert-butyl-4-hydroxybenzyl) isocyanurate and 1,3,5-tris(3-hydroxy-4-tert-butyl-2,6-dimethylbenzyl) isocyanurate; or is an organophosphorus stabilizer selected from the group consisting of tris(2,4-di-tert-butylphenyl) phosphite, bis(2,4-di-tert-butyl-6-methylphenyl) ethyl phosphite, 2,2',2"-nitrilo[triethyl-tris-(3,3',5,5'-tetra-tert-butyl-1,1'-biphenyl-2,2'-diyl) phosphite], tetrakis(2,4-di-butylphenyl) 4,4'-biphenylenediphosphonite, tris(nonylphenyl) phosphite, bis(2,4-di-tert-butylphenyl) pentaerythrityl diphosphite, 2,2'-ethylidenebis(2,4-di-tert-butylphenyl) fluorophosphite and 2-butyl-2-ethylpropan-1,3-diyl 2,4,6-tri-tert-butylphenyl phosphite; or is 5,7-di-tert-butyl-3-(3,4-dimethylphenyl)-2H-benzofuran-2-one; or is N,N-dialkylhydroxyl-amine made by the direct oxidation of N,N-di(hydrogenated tallow)amine; or is a hindered amine selected from the group consisting of bis(2,2,6,6-tetramethylpiperidin-4-yl) sebacate, the polycondensation product of 1-(2-hydroxyethyl)-2,2,6,6-tetramethyl-4-hydroxypiperidine and succinic acid, N,N',N",N"'-tetrakis[4,6-bis(butyl-1,2,2,6,6-pentamethylpiperidin-4-yl)amino-s-triazin-2-yl]-1,10-diamino-4,7-diazadecane, the polycondensation product of 4,4'-hexamethylenebis(amino-2,2,6,6-tetramethylpiperidine) and 2,4-dichloro-6-tert-octylamino-s-triazine, the polycondensation product of 4,4'-hexamethylenebis(amino-2,2,6,6-tetramethylpiperidine) and 2,4-dichloro-6-morpholino-s-triazine, the polycondensation product of 4,4'-hexamethylenebis(amino-1,2,2,6,6-pentamethylpiperidine) and 2,4-dichloro-6-morpholino-s-triazine, 2,2,6,6-tetramethylpiperidin-4yl octadecanoate, 3-dodecyl-1-(1-acetyl-2,2,6,6-tetramethylpiperidin-4-yl)-pyrrolidin-2,5-dione, 1,3,5-tris{N-cyclohexyl-N-[2-(2,2,6,6-tetramethylpiperazin-3-on-4-yl)ethyl]amino}-s-triazine, poly[methyl 3-(2,2,6,6-tetramethylpiperidin-4-yloxy)propyl]siloxane, the polycondensation product of 2,4-dichloro-6-(2,2,6,6-tetramethylpiperidin-4-yl)butylamino)-s-triazine, 2,2'ethylene-bis {[2,4-(2,2,6,6-tetramethylpiperidin-4-yl)butylamino-s-triazin-6-yl] aminotrimethyleneamino}, oligomer of N-{[2-(N-2,2,6,6-tetramethylpiperidin-4-yl)butylamino]-s-triazin-4-yl}-N,N'-bis(2,2,6,6-tetramethylpiperidin-4-yl)-1,6-hexanediamine terminated with 2,4-bis(dibutylamino)-s-triazin-6-yl, N,N',N"-tris {2,4-bis[N-(1,2,2,6,6-pentamethylpiperidin-4-yl)butylamino]-s-triazin-6-yl}-3,3'-ethylenediiminodipropylamine, N,N',N"'-tris{2,4-bis[N-(1,2,2,6,6-pentamethylpiperidin-4-yl)butylamino]-s-triazin-6-yl}-3,3'-ethylenediiminodipropylamine and N,N',N",N"'-tetrakis {2,4-bis[N-(1,2,2,6,6-pentamethylpiperidin-4-yl)butylamino]-s-triazin-6-yl}-3,3'-ethylenediiminodipropylamine; or is another N-hydrocarbyloxy substituted hindered amines selected from the group consisting of bis(1-octyloxy-2,2,6,6-tetramnethylpiperidin-4-yl) sebacate, bis(1-octyloxy-2,2,6,6-tetramethylpiperidin-4-yl) adipate, bis(1-cyclohexyloxy-2,2,6,6-tetramethylpiperidin-4-yl) adipate, bis(1-cyclohexyloxy-2,2,6,6-tetramethylpiperidin-4-yl) sebacate, 1-cyclohexyloxy-2,2,6,6-tetramethylpiperidin-4-yl octadecanoate, N,N',N"-tris {2,4-bis[N-(1-cyclohexyloxy-2,2,6,6-tetramethylpiperidin-4-yl)butylamino]-s-triazin-6-yl}-3,3'-ethylenediiminodipropylamine, N,N',N"'-tris {2,4-bis[N-(1-cyclohexyloxy-2,2,6,6-tetramethylpiperidin-4-yl) butylamino]-s-triazin-6-yl}-3,3'-ethylenediiminodipropylamine and N,N',N",N"'-tetrakis {2,4-bis[N-(1-cyclohexyloxy-2,2,6,6-tetramethylpiperidin-4-yl)butylamino]-s-triazin-6-yl }-3,3'-ethylenediimino-dipropylamine; or a hydroxy substituted N-hydrocarbyloxy substituted hindered amine selected from the group consisting of bis[1-(2 -hydroxy-2-methylpropoxy)-2,2,6,6-tetramethylpiperidin-4-yl)] sebacate; a mixture of bis[1-(2-hydroxy-2-methylpropoxy)-2,2,6,6-tetramethylpiperidin-4-yl] glutarate and bis[1-(2-hydroxy-2-methylpropoxy)-2,2,6,6-tetramethylpiperidin-4-yl] adipate; 1-(2-hydroxy-2-methylpropoxy)-4-octadecanoyloxy-2,2,6,6-tetramethylpiperidine; bis[1-(2-hydroxy-2-methylpropoxy)-2,2,6,6-tetramethylpiperidin-4-yl] adipate; bis[1-(2-hydroxy-2-methylpropoxy)-2,2,6,6-tetramethylpiperidin-4-yl] glutarate; bis[1-(2-hydroxy-2-methylpropoxy)-2,2,6,6-tetramethylpiperidin-4-yl] succinate; a mixture of bis[1-(2-hydroxy-2-methylpropoxy)-2,2,6,6-tetramethylpiperidin-4-yl] glutarate and bis[1-(2-hydroxy-2-methylpropoxy)-2,2,6,6-tetramethylpiperidin-4-yl] succinate; 1-(4-octadecanoyloxy-2,2,6,6-tetramethylpiperidin-1-yloxy)-2-octadecanoyloxy-2-methylpropane; 1-(2-hydroxy-2-methylpropoxy)-4-[9-(methoxy-carbonyl)nonanoyloxy]-2,2,6,6-tetramethylpiperidine; 1-(2-hydroxy-2-methylpropoxy)-4-[5-(methoxy-carbonyl)pentanoyloxy]-2,2,6,6-tetramethylpiperidine; 1-(2-hydroxy-2-methylpropoxy)-4-[3-(methoxy-carbonyl)propionyloxy]-2,2,6,6-tetramethylpiperidine; 1-(2-hydroxy-2-methylpropoxy)-4-[4-(methoxy-carbonyl)butyryloxy]-2,2,6,6-tetramethylpiperidine; or is a UV absorber selected from the group consisting of 2-(2-hydroxy-3,5-di-α-cumylphenyl)-2H-benzotriazole, 2-(2-hydroxy-5-methylphenyl)-2H-benzotriazole, 5-chloro-2-(2-hydroxy-3,5-di-tert-butylphenyl)-2H-benzotriazole, 2-(2-hydroxy-3,5-di-tert-amylphenyl)-2H-benzotriazole, 2-(2-hydroxy-3-α-cumyl-5-tert-octylphenyl)-2H-benzotriazole, 2,4-di-tert-butylphenyl 3,5-di-tert-butyl4-hydroxybenzoate, 2-hydroxy-4-n-octyloxybenzophenone, 2,4-bis(2,4-dimethylphenyl)-6-(2-hydroxy-4-octyloxyphenyl)-s- triazine, oligomer of N-{2-[(1-propoxy-2,2,6,6-tetramethylpiperidin-4-yl)butylamino]-s-triazin-4-yl }-N,N'-bis(1-propoxy-2,2,6,6-tetramethylpiperidin-4-yl)-1,6-hexanediamine terminated with 2,4-bis(dibutylamino)-s-triazin-6-yl, the condensation product of 2-morpholino-4,6-dichloro-s-triazine with N,N'-bis(1,2,2,6,6-pentamethylpiperidin-4-yl)-1,6-hexanediamine; or mixtures thereof.

Preferably the coadditive stabilizer is neopentanetetrayl tetrakis(3,5-di-tert-butyl-4-hydroxyhydrocinnamate, tris(2,4-di-tert-butylphenyl)phosphite, N,N-dialkylhydroxylamine made by the direct oxidation of N,N-di(hydrogenated tallow)amine, N,N',N'',N'''-tetrakis[4,6-bis(butyl-1,2,2,6,6-pentamethylpiperidin-4 -yl)amino-s-triazin-2-yl]-1,10-diamino-4,7-diazadecane, the polycondensation product of 4,4'-hexamethylene-bis(amino-2,2,6,6-tetramethyl-piperidine) and 2,4-dichloro-6-tert-octylamino-s-triazine, the polycondensation product of 4,4'-hexamethylenebis (amino-2,2,6,6-tetramethylpiperidine) and 2,4-dichloro-6-morpholino-s-triazine, the polycondensation product of 4,4'-hexamethylenebis(amino-1,2,2,6,6-pentamethylpiperidine) and 2,4-dichloro-6-morpholino-s-triazine, oligomer of N-{[2-(N-2,2,6,6-tetramethylpiperidin-4-yl)butylamino]-s-triazin-4-yl}-N,N'-bis(2,2,6,6-tetramethylpiperidin-4-yl)-1,6-hexanediamine terminated with 2,4-bis(dibutylamino)-s-triazin-6-yl, N,N',N''-tris {2,4-bis[N-(1,2,2,6,6-pentamethylpiperidin-4-yl)butylamino]-s-triazin-6-yl}-3,3'-ethylenediiminodipropylamine, N,N',N'''-tris {2,4-bis[N-(1,2,2,6,6-pentamethylpiperidin-4-yl)butylamino]-s-triazin-6}-yl)-3,3'-ethylenediiminodipropylamine and N,N',N'',N'''-tetrakis {2,4-bis[N-(1,2,2,6,6-pentamethylpiperidin-4-yl)butylamino]-s-triazin-6-yl}-3,3'-ethylene-diiminodipropylamine, oligomer of N-{2-[(1-propoxy-2,2,6,6-tetramethylpiperidin-4-yl)butylamino]-s-triazin-4-yl}-N,N'-bis(1-propoxy-2,2,6,6-tetramethylpiperidin-4-yl)-1,6-hexanediamine terminated with 2,4-bis(dibutylamino)-s-triazin-6-yl, or the condensation product of 2-morpholino-4,6-dichloro-s-triazine with N,N'-bis(1,2,2,6,6-pentamethylpiperidin-4-yl)-1,6-hexanediamine.

The alkyd resin lacquers which can be stabilized against the action of light and moisture in accordance with the instant invention are the conventional stoving lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99–123). Other crosslinking agents include glycouril resins, blocked isocyanates or epoxy resins.

The lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or iso-cyanurates. The epoxy and epoxy-polyester resins are crosslinked with conventional cross-linkers such as acids, acid anhydrides, amines and the like. Correspondingly, the epoxide may be utilized as the crosslinking agent for various acrylic or polyester resin systems that have been modified by the presence of reactive groups on the backbone structure.

When used in two-coat finishes, the compounds of the instant invention can be incorporated in the clear coat or both in the clear coat and in the pigmented base coat.

When water-soluble, water miscible or water dispersible coating are desired ammonium salts of acid groups present in the resin are formed. Powder coating composition can be prepared by reacting glycidyl methacrylate with selected alcohol components.

The instant benzotriazoles are made by conventional methods for preparing such compounds. The usual procedure involves the diazotization of a substituted o-nitroaniline followed by coupling the resultant diazonium salt with a substituted phenol and reduction of the azobenzene intermediate to the corresponding desired benzotriazole. The starting materials for these benzotriazoles are largely items of commerce or can be prepared by normal methods of organic synthesis.

While the instant benzotriazoles with their enhanced durability are particularly suited for automotive coating applications, it is contemplated that they will also be espeically useful in other applications where their enhanced durability is required such as in solar films and the like.

The following examples are meant for illustrative purposes only and are not to be construed to limit the instant invention in any manner whatsoever.

EXAMPLE 1

4-Methoxy-α-methylstyrene

To a 1000 mL three-necked flask equipped with a mechanical stirrer, methyl magnesium bromide/diethyl ether solution (200 mL, 3.0 mol) is added. A solution of 85.3 g of 4'-methoxyacetophenone dissolved in 80 mL of anhydrous diethyl ether is charged to the Grignard reagent over 90 minutes at ambient temperature. Diethyl ether (200 mL) and 250 mL of 3N hydrochloric acid are added slowly to the reaction mixture. The solution is stirred for another 30 minutes. The aqueous layer is separated and washed twice with 100 mL of diethyl ether. The ethereal layers are combined and vacuum distilled. The desired product is obtained in a yield of 91.7 g as a yellow oil whose structure is verified by $^1$Hnmr and mass spectroscopy.

EXAMPLE 2

α-Methylstyrene Derivatives

When following the general procedure of Example 1, the following α-methylstyrene derivatives are made when 4'-methoxyacetophenone is replaced with the corresponding substituted acetophenone intermediate.
2-methoxy-α-methylstyrene
3-methoxy-α-methylstyrene
2-fluoro-α-methylstyrene
3-fluoro-α-methylstyrene
4-fluoro-α-methylstyrene
2-chloro-α-methylstyrene
3-chloro-α-methylstyrene
4-trifluoromethyl-α-methylstyrene

EXAMPLE 3

2-(4-Methoxy-α-cumyl)-4-tert-butylphenol

To a three-necked 500 mL flask equipped with a mechanical stirrer, 37 g of 4-tert-butylphenol, 100 mL of toluene and 2.4 g of p-toluenesulfonic acid are charged and heater to 55° C. The 4-methoxy-α-methylstyrene (40 g) prepared in Example 1 is added over 2.5 hours. The reaction mass is stirred for an additional three hours at 65° C. The reaction mass is then washed twice with 200 mL of saturated sodium bicarbonate solution and thrice with 100 mL of water. The solvent is removed by vacuum distillation and unreacted phenol and alkene are moved by Kugelrohr distillation at 100° C./0.16 mm Hg. The title compound is prepared in a yield of 78 g as a light brown oil whose structure is consistent with $^1$Hnmr and mass spectroscopy.

EXAMPLE 4

2-(4-Fluoro-α-cumyl)-4-tert-octylphenol

4-Fluoro-α-methylstyrene (18 g) as prepared in Example 2 and 20.6 g of 4-tert-octylphenol are reacted according to the procedure of Example 3 to yield 26 g of the title compound as a reddish, viscous oil whose structure is consistent with $^1$Hnmr and mass spectroscopy.

EXAMPLE 5

2-(4-Chloro-α-cumyl)-4-tert-butylphenol

4-Chloro-α-methylstyrene (50 g) and 45 g of 4-tert-butylphenol are reacted according to the procedure of Example 3 to afford the title compound in a yield of 66.6 g as a colorless oil. The structure is confirmed by $^1$Hnmr and mass spectroscopy.

EXAMPLE 6

2,4-Di-(4-chloro-α-cumyl)phenol

The title compound is prepared according to the procedure of Example 3 by reacting 19 g of phenol with 80 g of 4-chloro-α-methylstyrene to give 53.4 g of the title compound as a white solid. The structure is confirmed by $^1$Hnmr and mass spectroscopy.

EXAMPLE 7

2,4-Di-(4-methoxy-α-cumyl)phenol

The title compound is prepared according to the procedure of Example 3 by reacting 23.5 g of phenol with 96 g of 4-methoxy-α-methylstyrene to give 53 g of the title compound as a white solid. The structure is confirmed by $^1$Hnmr and mass spectroscopy.

EXAMPLE 8

4-Trifluoromethyl-2-nitrobenzenediazonium Bisulfate

To a 500 mL three-necked flask fitted with a mechanical stirrer are added 40 g of 40% nitrosylsulfuric acid and 120 g of concentrated sulfuric acid. 4-Trifluoro-2-nitroaniline (=4-amino-3-nitrobenzotrifluoride) (25 g) is charged portionwise so as to maintain a temperature of less than 30° C. The resulting solution is then stored at 0° C. until use.

EXAMPLE 9

4-Trifluoromethyl-2-nitrobenzenediazonium Bisulfate

To a 500 mL three-necked flask fitted with a mechanical stirrer are added 99.5 g of concentrated sulfuric acid and 62.5 g of 4-trifluoro-2-nitroaniline (=4-amino-3-nitrobenzotrifluoride). After heating to 75° C., 200 g of water is added at which time the temperature is reduced to 0° C. Sodium nitrite (52.9 g, 40 wt %) is added over two hours while maintaining the solution at 0–5° C. The diazonium salt solution (351 g) is then filtered and stored at −15° C. until use.

EXAMPLE 10

2-Nitrobenzenediazonium Bisulfate

To a 500 mL three-necked flask fitted with a mechanical stirrer are added 65 g of concentrated sulfuric acid and 41.4 g of 2-nitroaniline. After heating to 75° C., 164 g of water is added at which time the temperature is reduced to 0° C. Sodium nitrite (54 g, 40 wt %) is added over two hours while maintaining the solution at 0–5° C. The diazonium salt solution (292 g) is then filtered and stored at −15° C. until use.

EXAMPLE 11

4-Chloro-2-nitrobenzenediazonium Chloride

To a 500 mL three-necked flask fitted with a mechanical stirrer are added 134.2 g of concentrated hydrochloric acid and 60 g of 4-chloro-2-nitroaniline. After heating to 65° C., 106.6 g of water is added at which time the temperature is reduced to 0° C. Sodium nitrite (63.4 g, 40 wt %) is slowly added to the slurry while maintaining the solution at 0° C. The diazonium salt solution (281 g) is then filtered and stored at −15° C. until later use.

EXAMPLE 12

5-Trifluoromethyl-2-nitro-2'-hydroxy-3'-(4-methoxy-α-cumyl)-5'-tert-butylazobenzene To a 1 L three-necked flask equipped with a mechanical stirrer, 33 g of 2-(4-methoxy-α-cumyl)-4-tert-butylphenol prepared in Example 3, 2 g of PETROSUL® M-60 and 85 mL of xylenes are added. After dissolution of the phenol, the solution is cooled to 10–15° C. at which time the diazonium salt prepared in Example 8 is charged over a three hour period. The reaction mass is agitated an additional three hours at 25–30° C. The aqueous layer is separated and the organic layer is vacuum distilled. The desired product is obtained in a 50 g yield as a dark red solid whose structure is consistent by $^1$Hnmr.

EXAMPLE 13

5-Trifluoromethyl-2-[2-hydroxy-3-(4-methoxy-α-cumyl)-5-tert-butylphenyl]-2H-benzotriazole To a 2 L, five-necked flask equipped with a mechanical stirrer, 500 mL of 2-butanol and 8 g of sodium hydroxide pellets are charged and heated to 90° C. A solution of 50 g of the monoazo compound prepared in Example 12, 2.3 g of 2,3-dichloro-1,4-naphthoquinone and 300 mL of heptane is charged to the hot butanol solution over a three hour period. After the addition is complete, the reaction mass is stirred for an additional hour at reflux. To the reaction mass is then added, 100 mL of water and the pH is adjusted to 2 with 30% aqueous sulfuric acid. The aqueous layer is removed and the organic layer is washed once with 100 mL of saturated sodium chloride solution and twice with water. The desired product is crystallized from the solution yielding the title compound as a light yellow solid melting at 140° C. The structure is verified by $^1$Hnmr and mass spectroscopy analyses.

EXAMPLE 14

5-Trifluoromethyl-2-nitro-2'-hydroxy-3'-(4-fluoro-α-cumyl)-5'-tert-octylazobenzene The title compound is prepared according to the procedure of Example 12 from 24 g of 2-(4-fluoro-α-cumyl)-4-tert-octylphenol prepared in Example 4 and 126 g (ca. 21.5%) of the aqueous diazonium salt solution of Example 9. The title compound is obtained as a crimson red oil (51.4 g) which still contains some traces of solvent. The structure is consistent by $^1$Hnmr.

EXAMPLE 15

5-Trifluoromethyl-2-[2-hydroxy-3-(4-fluoro-α-cumyl)-5-tert-octylphenyl]-2H-benzotriazole-N-oxide To a 500 mL three-necked flask fitted with a mechanical stirrer are charged 51.4 g of the crude monoazo compound prepared in Example 14, 50 g of xylenes, 0.5 g of 5% palladium on carbon catalyst and 85 g of n-butylamine. This solution is cooled to 10° C. and 3.8 g of hydrazine is added slowly over two hours while not allowing the temperature to rise above 20° C. The catalyst is removed by filtration and the solvent is vacuum distilled. The title compound is then crystallized from methanol. After vacuum drying, 20.6 g of the desired product is obtained as an orange solid melting at 146–149° C. The structure is verified by $^1$Hnmr, $^{19}$Fnmr and mass spectroscopy.

EXAMPLE 16

5-Trifluoromethyl-2-[2-hydroxy-3-(4-fluoro-α-cumyl)-5-tert-octylphenyl]-2H-benzotriazole To a 500 mL three-necked flask equipped with a mechanical stirrer, 3.7 g of sodium hydroxide pellets and 50 mL of 2-butanol are charged and heated to 83° C. To this solution is added over a 90-minute period a solution of 230 mL of methyl ethyl ketone, 20 g of the benzotriazole-N-oxide prepared in Example 15 and 0.85 g of 2,3-dichloro-1,4-naphthoquinone. The mixture is refluxed at 88° C. for one hour while distilling off methyl ethyl ketone. After cooling down to ambient temperature, 25 g of water and 30 mL of ethyl acetate are added at which time the pH is reduced to 3 with 30% aqueous sulfuric acid. After splitting off the aqueous layer, the solvent is removed by distillation. The crude solid is purified by silica gel chromatography using heptane/ethyl acetate (49/1) as eluent. After collecting the desired fractions and crystallizing from methanol/toluene, the title compound is obtained in a yield of 14 g as a light yellow solid melting at 120–122° C. The structure is consistent with analyses by $^1$Hnmr, $^{19}$Fnmr and mass spectroscopy.

EXAMPLE 17

2-Nitro-2'-hydroxy-3'-(4-methoxy-α-cumyl)-5'-tert-butylazobenzene

The title compound is prepared according to the procedure of Example 12 using 36 g of 2-(4-methoxy-α-cumyl)-4-tert-butylphenol prepared in Example 3 and 130 g of the diazonium salt solutions (ca. 23% solution) prepared in Example 10. The title compound is obtained in a yield of 60 g as a crimson red oil whose structure is consistent with $^1$Hnmr analysis.

EXAMPLE 18

2-[2-Hydroxy-3-(4-methoxy-α-cumyl)-5-tert-butylphenyl]-2H-benzotriazole-N-oxide

The title compound is prepared in a yield of 56.8 g according to the procedure of Example 15 using 60 g of the monoazo derivative prepared in Example 17.

EXAMPLE 19

2-[2-Hydroxy-3-(4-methoxy-α-cumyl)-5-tert-butylphenyl]-2H-benzotriazole

The title compound is prepared according to the procedure given in Example 16 using 56 g of the N-oxide compound of Example 18. The desired product is obtained in a yield of 13.2 g as a white solid melting at 139–140° C. The structure is verified by $^1$Hnmr and mass spectroscopy analyses.

EXAMPLE 20

2-Nitro-2'-hydroxy-3'-(4-chloro-α-cumyl)-5'-tert-butylazobenzene

The title compound is prepared according to the method given in Example 12 using 45 g of 2-(4-chloro-α-cumyl)-4-tert-butylphenol prepared in Example 5 and 161 g of the diazonium salt solution (ca. 23%) prepared in Example 10. The desired compound is prepared in a yield of 70 g as a crimson viscous oil.

EXAMPLE 21

2-[2-Hydroxy-3-(4-chloro-α-cumyl)-5-tert-butylphenyl]-2H-benzotriazole-N-oxide

The title compound is prepared according to the method of Example 15 using 70 g of the monoazo compound of Example 20. The title compound is obtained in a yield of 12.8 g as a solid melting at 136–141° C. The structure is consistent by $^1$Hnmr and mass spectroscopy analyses.

EXAMPLE 22

2-[2-Hydroxy-3-(4-chloro-α-cumyl)-5-tert-butylphenyl]-2H-benzotriazole

The title compound is prepared according to the procedure of Example 16 using 10 g of the N-oxide prepared in Example 21. The product is obtained in a yield of 7.7 g as a solid melting at 153–155° C. The structure is confirmed by $^1$Hnmr and mass spectroscopy.

EXAMPLE 23

5-Chloro-2-nitro-2'-hydroxy-3'-(4-chloro-α-cumyl)-5'-tert-butylazobenzene

To a 500 mL three-necked flask equipped with a mechanical stirrer are added 43.6 g of 2-(4-chloro-α-cumyl)-4-tert-butylphenol prepared in Example 5, 167 g of methanol, 27.8 g of sodium hydroxide pellets and 11 g of water. The solution is cooled to −15° C. and 168 g of the diazonium salt solution prepared in Example 11 is slowly added over three hours. The crimson slurry is acidified to pH 2–3 with dilute hydrochloric acid. The monoazo title compound is filtered and washed with water. The crude cake is oven dried to yield 77.5 g of crimson red solid which still contains some residual sodium chloride. This product has a melting point of 195–197° C. The structure is verified by $^1$Hnmr and mass spectroscopy.

EXAMPLE 24

5-Chloro-2-[2-hydroxy-3-(4-chloro-α-cumyl)-5-tert-butylphenyl]-2H-benzotriazole-N-oxide The title compound is prepared according to the method given in Example 15 using 31 g of the monoazo compound

EXAMPLE 25

5-Chloro-2-[2-hydroxy-3-(4-chloro-α-cumyl)-5-tert-butylphenyl]-2H-benzotriazole

The title compound is prepared according to the procedure of Example 16 using 14 g of the N-oxide prepared in Example 24 to give 10.5 g of the desired product as a light yellow solid melting at 130–131° C. The structure is confirmed by $^1$Hnmr and mass spectroscopy analyses.

EXAMPLE 26

5-Chloro-2-nitro-2'-hydroxy-3',5'-di-(4-chloro-α-cumyl)azobenzene

The title compound is prepared according to the procedure of Example 23 using 45 g of 2,4-di-(4-chloro-α-cumyl) phenol prepared in Example 6 and 138 g of the diazonium salt solution prepared in Example 11 in a yield of 66.3 g. The desired product is a crimson red solid containing some residual salt and melts at 163–165° C. The structure is confirmed by $^1$Hnmr and mass spectroscopy analyses.

EXAMPLE 27

5-Chloro-2-[2-hydroxy-3,5-di-(4-chloro-α-cumyl) phenyl]-2H-benzotriazole-N-oxide The title compound is prepared according to the procedure of Example 15 using 35 g of the monoazo compound prepared in Example 26. The title compound is obtained in a yield of 18.6 g as an orange solid melting at 189–190° C. The structure is confirmed by $^1$Hnmr and mass spectroscopy analyses.

EXAMPLE 28

5-Chloro-2-[2-hydroxy-3,5-di-(4-chloro-α-cumyl) phenyl]-2H-benzotriazole

The title compound is prepared by the method given in Example 16 using 15 g of the N-oxide compound prepared in Example 27. The desired product is obtained in a yield of 14.3 g as a light yellow solid melting at 155–157° C. The structure is confirmed by $^1$Hnmr and mass spectroscopy analyses.

EXAMPLE 29

5-Chloro-2-nitro-2'-hydroxy-3',5'-di-(4-methoxy-α-cumyl)azobenzene

The title compound is prepared according to the procedure of Example 23 using 45 g of 2,4-di-(4-methoxy-α-cumyl)phenol prepared in Example 7 and 131 g of the diazonium salt solution of Example 11. The desired product is obtained in a yield of 49.1 g as a crimson red solid melting at 150–152° C. The structure is confirmed by $^1$Hnmr and mass spectroscopy analyses.

EXAMPLE 30

5-Chloro-2-[2-hydroxy-3,5-di-(4-methoxy-α-cumyl) phenyl]-2H-benzotriazole-N-oxide The title compound is prepared according to Example 15 using 25 g of the monoazo compound of Example 29. The desired product is obtained in a yield of 19.9 g as an orange solid melting at 155–162° C. The structure is confirmed by $^1$Hnmr and mass spectroscopy analyses.

EXAMPLE 31

5-Chloro-2-[2-hydroxy-3,5-di-(4-methoxy-α-cumyl) phenyl]-2H-benzotriazole

The title compound is prepared according to the method of Example 16 using 11.5 g of the N-oxide compound made in Example 30. The desired product is obtained in a yield of 10 g as a light yellow solid melting at 58–68° C. The structure is confirmed by $^1$Hnmr and mass spectroscopy analyses.

EXAMPLE 32

5-Trifluoromethyl-2-[2-hydroxy-3-(4-chloro-α-cumyl)-5-tert-butylphenyl]-2H-benzotriazole Following the general procedure of Example 13, starting with the substituted phenol prepared in Example 5 and the diazonium salt prepared in Example 8, the title compound is prepared as a light yellow solid melting at 129–132° C. The structure is confirmed by $^1$Hnmr, $^{19}$Fnmr and mass spectroscopy analyses.

EXAMPLE 33

5-Chloro-2-[2-hydroxy-3-(4-methoxy-α-cumyl)-5-tert-butylphenyl]-2H-benzotriazole Following the general procedure of Example 13, starting with the substituted phenol prepared in Example 3 and the diazonium salt prepared in Example 11, the title compound is prepared as a light yellow solid melting at 121–122° C. The structure is confirmed by $^1$Hnmr and mass spectroscopy analyses.

EXAMPLE 34a

2-[2-Hydroxy-3-(4-chlorosulfonyl-α-cumyl)-5-tert-octylphenyl]-2H-benzotriazole 2-(2-Hydroxy-3-α-cumyl-5-tert-octylphenyl)-2H-benzotriazole (60.5 g) is dissolved in 200 mL of 1,2-dichloroethane and dried by distilling off 25 mL of solvent using a Dean-Stark trap under nitrogen. The trap is replaced with a condenser and the solution is heated to reflux. While at reflux, the nitrogen feed is replaced by a drying tube and a solution of 200 g of chlorosulfonic acid in 100 mL of 1,2-dichloroethane is added dropwise from an addition funnel over a 45-minute period. The reaction mixture is stirred at reflux for an additional 30 minutes, then cooled to room temperature and pured over 1400 mL of ice and water to form a thick white emulsion. Salt and 1000 mL of ethyl acetate are added and the mixture is separated with the organic layer being dried over anhydrous sodium sulfate. The organic solution is concentrated to yield 67.8 g of a thick brown oil. Separation by chromatography on silica gel with heptane/ethyl acetate 6/1 as eluent, followed by recrystallization from heptane/ethyl acetate affords 18.0 g of the title compound as light yellow crystals melting at 166–168° C. The structure of the compound is confirmed by $^1$Hnmr and mass spectroscopic analyses.

EXAMPLE 34b

2-{2-Hydroxy-3-[4-(2-dimethylaminoethyl) aminosulfonyl-α-cumyl]-5-tert-octylphenyl}-2H-benzotriazole The title compound is prepared according to the procedure given in instant Example 35 using 8.0 g of the intermediate compound prepared in Example 34a and 1.4 g of 2-dimethylaminoethylamine. After several recrystallizations from ethyl acetate and ethyl acetate/heptane mixtures, 5.6 g of the title compound is prepared as a near white solid melting at 118–120° C. The structure of the compound is confirmed by $^1$Hnmr and mass spectroscopy analyses.

EXAMPLE 35

2-{2-hydroxy-3-[4-(3-dimethylaminopropyl) aminosulfonyl-α-cumyl]-5-tert-octylphenyl}-2H-benzotriazole A solution of 8.0 g of the intermediate prepared in instant Example 34a in 50 mL of methylene chloride is added dropwise to a stirred solution of 1.5 g of 3-dimethylaminopropylamine, 5 g of triethylamine and 5 mL of methylene chloride at 0° C. to 5° C. over a 30 minute period. The reaction mixture turns yellow and some white precipitate forms. The mixture is allowed to warm to room temperature and is then washed three times with brine. An additional 5 mL of triethylamine is added between the brine washings. The organic layer is dried over anhydrous sodium sulfate and is then concentrated to give 9.2 g of a yellow oil which solidifies on standing. Heptane is added and the mixture is reconcentrated to drive off any residual triethylamine. The product is recrystallized from heptane/toluene to afford 8.4 g of the title compound as a near white solid melting at 96–101° C. The structure of the compound is confirmed by $^1$Hnmr and mass spectroscopic analyses.

EXAMPLE 36

Polycarbonate

The durability of representative instant benzotriazoles in thermoplastic substrates is determined by incorporating various test compounds into solvent cast films of polycarbonate resins. The free standing films are mounted into cardboard holders, secured in metal frames and exposed in an Atlas $C_{165}$ Xenon-arc Weather-Ometer under dry conditions according to ASTM $G_{26}$. Loss of UV absorber is determined by monitoring the loss of diagnostic UV absorption.

Polycarbonate flake (LEXAN® 145, General Electric) is dissolved in methylene chloride at room temperature along with between 1 and 3% by weight of test benzotriazole, based on the polycarbonate. Films are cast using a calibrated drawdown bar to prepare 1 mil thick film after drying.

| Compound of Example* (% by weight) | Change in Initial Absorbance after 750 hours |
|---|---|
| TINUVIN ® 234* (2.50%) | 0.18 |
| Example 13 (2.70%) | 0.03 |
| Example 32 (2.72%) | 0.08 |
| Example 22 (2.34%) | 0.06 |

*TINUVIN ® 234 is 2-(2-hydroxy-3,5-di-α-cumylphenyl)-2H-benzotriazole.

These data show that the instant compounds are particularly efficacious when used in thermoplastic compositions, such as polycarbonate, even surpassing a commercial UV absorber in effectiveness. This is shown by the reduction in absorbance loss after exposure to actinic radiation.

EXAMPLE 37

Polycarbonate

Polycarbonate films of about 1 mil thickness and containing a UV absorber are prepared by dissolving polycarbonate granules (LEXAN® 145, General Electric) and UV absorbers in methylene chloride and casting the films on a glass plate using a drawdown bar. The films are exposed for 750 hours in a Xenon Arc Weather-Ometer according to ASTM $G_{26}$ test method and the color change (ΔYI) versus that for unexposed films are recorded below. The color measurements (yellowness index —YI) are carried out on an ACS spectrophotometer, small area view, spectral component included d/8, D65, 10° observer, YI 1925 for unexposed and exposed samples after 750 hours.

| Compound of Example* (% by weight) | ΔYI |
|---|---|
| Blank (no stabilizer) | 12.30 |
| TINUVIN ® 234 (2.50%) | 2.28 |
| Example 22 (2.34%) | 1.93 |
| Example 19 (2.32%) | 1.80 |
| Example 32 (2.72%) | 1.52 |
| Example 13 (2.70%) | 1.38 |

*TINUVIN ® 234 is 2-(2-hydroxy-3,5-di-α-cumylphenyl)-2H-benzotriazole.

These data show that the instant compounds are particularly efficacious when used in thermoplastic compositions, such as polycarbonate, even surpassing a commerical UV absorber in effectiveness. This is shown by the reduction of yellowing (ΔYI) after exposure to actinic radiation.

EXAMPLE 38

Poly(methyl methacrylate)

The durability of representative instant benzotriazoles in thermoplastic substrates is determined by incorporating various test compounds into solvent cast films of a poly (methyl methacrylate) (PMMA) resin. The free standing films are mounted into cardboard holders, secured in metal frames and exposed in an Atlas C165 Xenon-arc Weather-Ometer under dry conditions according to ASTM $G_{26}$. Loss of UV absorber is determined by monitoring the loss of diagnostic UV absorption as described earlier. Performance is measured by a change in color or the physical integrity of the film, or in loss of absorbance of the UV absorber at λmax.

Poly(methyl methacrylate), medium molecular weight, Aldrich, is dissolved in methylene chloride at room temperature along with between 1 and 3% by weight of test benzotriazole, based on the PMMA resin. Films are cast using a calibrated drawdown bar to prepare 1 mil thick film after drying.

| Compound of Example* (% by weight) | Change in Initial Absorbance after 750 hours |
|---|---|
| TINUVIN ® 234* (2.50%) | 0.18 |
| Example 25 (2.54%) | 0.15 |
| Example 28 (3.07%) | 0.07 |
| Example 31 (3.03%) | 0.10 |
| Example 32 (2.72%) | 0.02 |

*TINUVIN ® 234 is 2-(2-hydroxy-3,5-di-α-cumylphenyl)-2H-benzptriazole.

These data show that the instant compounds are particularly efficacious when used in thermoplastic compositions, such as poly(methyl methacrylate), even surpassing a commercial UV absorber in effectiveness. This is shown by the reduction in absorbance loss after exposure to actinic radiation.

EXAMPLE 39

Incorporation into Photographic Layers

A gelatin coat of the following composition (per m$^2$) is applied in the customary manner to a polyester base.

| Components | Amount |
| --- | --- |
| Gelatin | 1200 mg |
| Tricresyl Phosphate | 510 mg |
| Hardener* | 40 mg |
| Wetting Agent** | 100 mg |
| Test UV Absorber | 400 mg |

*potassium salt of 2-hydroxy-4,6-dichloro-s-triazine
**sodium 4,8-diisobutylnaphthalene-2-sulfonate The gelatin coats are dried at 20° C. for seven days.

When the instant UV absorbers are used, clear transparent coats are obtained which are suitable for photographic recording material for example as a UV filter coat.

| | % Change in Initial Optical Density (2.0) after | |
| --- | --- | --- |
| Test Compound | 60 KJ Exposure | 120 KJ Exposure |
| TINUVIN ® 328 | 19 | 66 |
| Example 25 | 2 | 6 |
| Example 33 | 1 | 5 |
| Example 32 | 1 | 4 |

TINUVIN ® 328 is 2-(2-hydroxy-3,5-di-tert-amylphenyl)-2H-benzotriazole.

These data show that the instant compounds when used in a photographic layer are extremely photostable.

EXAMPLE 40

Photographic Compositions

A polyethylene-coated base material is coated with a gelatin coat comprising silver bromide and a magenta coupler (M-9). The gelatin coat includes the following component (per m$^2$ of base material):

| Component | AgBr coat |
| --- | --- |
| Gelatin | 5.15 g |
| Hardener* | 300 mg |
| Wetting Agent** | 85 mg |
| Silver Bromide | 260 mg |
| Magenta Coupler (M-9) | 325 mg |
| Tricresyl Phosphate | 162 mg |

*potassium salt of 2-hydroxy-4,6-dichloro-s-triazine
**sodium 4,8-diisobutylnaphthalene-2-sulfonate
M-9 is 3-tridecyl-6-tert-butyl-7-chloro-1H-pyrazolo[4,2-d]pyrazole.

A step wedge having a density difference of 0.3 log E per step is exposed onto each of the resulting samples which are then processed in accordance with the manufacturer's instructions in the P94 process of Agfa Gevaert for negative color papers.

After exposure and processing, the density of reflectance in the green region for the magenta stage is measured at a density of between 0.9 and 1.1 of the wedge.

A UV absorber filter comprising an instant test benzotriazole is prepared on transparent base material as described in Example 39.

The wedge is subsequently exposed behind the UV absorber filter in an Atlas exposure instrument at 15 kJ/cm$^2$ and the reflectance density is measured again. The magenta dye density loss (−ΔD) is greatly reduced by the instant test compound as stabilizer in comparison with the sample containing no stabilizer.

EXAMPLE 41

Photographic Compositions

The procedure described in Example 39 is repeated using a mixture of 2 parts by weight of an instant test compound and 1 part by weight of an s-triazine UV absorber. Clear transparent coats are obtained which are suitable for a photographic recording material.

EXAMPLE 42

Photographic Compositions

A photographic material having the following layer structure is prepared:
top layer
red-sensitive layer
second gelatin layer
green-sensitive layer
first gelatin layer
blue-sensitive layer
polyethylene base
The gelatin layers consist of the following components (per m$^2$ of base material):
Blue-sensitive layer
α-(3-benzyl-4-ethoxyhydantoin-1-yl)-α-pivaloyl-2-chloro-5-[α-(2,4-di-tert-amylphenoxy)-acetanilide (400 mg)
α-(1-butylphenylurazol-4-yl)-α-pivaloyl-5-(3-dodecanesulfonyl-2-methylpropanamido)-2-methoxyacetamide (400 mg)
dibutyl phthalate (130 mg)
dinonyl phthalate (130 mg)
gelatin (1200 mg)
1,5-dioxa-3-ethyl-3-[β-(3,5-di-tert-butyl-4-hydroxyphenyl)propionyloxymethyl]-8,10-diphenyl-9-thia[5.5]spiroundecane (150 mg)
bis(1-acryloyl-2,2,6,6-tetramethyl-4-piperidyl) 2,2-bis(3,5-di-tert-butyl-4 -hydroxybenzyl)-malonate (150 mg)
3,5-di-tert-butyl-4-hydroxy(2,4-di-tert-amylphenyl) benzoate (150 mg)
poly(N-tert-butylacrylamide) (50 mg)
blue-sensitive silver chlorobromide emulsion (240 mg)
First gelatin interlayer
gelatin (1000 mg)
2,5-di-tert-octylhydroquinone (100 mg)
hexyl 5-[2,5-dihydroxy-4-(4-hexyloxycarbonyl-1,1-dimethylbutyl)phenyl]-5-methyl-hexanoate (100 mg)
dibutyl phthalate (200 mg)
diisobutyl phthalate (200 mg)
Green-sensitive layer
7-chloro-2-{2-[2-(2,4-di-tert-amylphenoxy)octanamido]-1-methylethyl }-6-methyl-1H-pyrazolo[1,5b][1,2,4]triazole (100 mg)
6-tert-butyl-7-chloro-3-(3-dodecanesulfonylpropyl)-1H-pyrazolo)-1H-pyrazolo[5,1o-][1,2,4]triazole (100 mg)
dibutyl phthalate (100 mg)
dicresyl phosphate (100 mg)
trioctyl phosphate (100 mg)
gelatin (1400 mg)

3,3,3',3'-tetramethyl-5,5',6,6'-tetrapropoxy-1,1'-spirobiindane (100 mg)
4-(isotridecyloxyphenyl)thiomorpholine-1,1-dioxide (100 mg)
4,4'-butylidenebis(3-methyl-6-tert-butylphenol) (50 mg)
2,2'-isobutylidenebis(4,6-dimethylphenol) (10 mg)
3,5-dichloro-4-(hexadecyloxycarbpnyloxy)ethylbenzoate (20 mg)
3,5-bis[3-(2,4-di-tert-amylphenoxy)propylcarbamoyl] sodium benzenesulfinate (20 mg)
green-sensitive silver chlorobromide emulsion (150 mg)
Second gelatin interlayer
gelatin (1000 mg)
5-chloro-2-(3,5-di-tert-butyl-2-hydroxyphenyl)benzo-1,2,3-triazole (200 mg)
2-(3-dodecyl-2-hydroxy-5-methylphenyl)benzo-1,2,3-triazole (200 mg)
trinonyl phosphate (300 mg)
2,5-di-tert-octylhydroquinone (50 mg)
hexyl 5-[2,5-dihydroxy-4-(4-hexyloxycarbonyl-1,1-dimethylbutyl)phenyl]-5-methylhexanoate (50 mg)
Red-sensitive layer
2-[α-(2,4-di-tert-amylphenoxy)butanamido]-4,6-dichloro-5-ethylphenol (150 mg)
2,4-dichloro-3-ethyl-6-hexadecanamidophenol (150 mg)
4-chloro-2-(1,2,3,4,5-pentafluorobenzamido)-5-[2-(2,4-di-tert-amylphenoxy)-3-methylbutanamido]phenol (100 mg)
dioctyl phthalate (100 mg)
dicyclohexyl phthalate (100 mg)
gelatin (1200 mg)
5-chloro-2-(3,5-di-tert-butyl-2-hydroxyphenyl)benzo-1,2,3-triazole (100 mg)
2-(3-dodecyl-2-hydroxy-5-methylphenyl)benzo-1,2,3-triazole (100 mg)
3,5-di-tert-butyl-4-hydroxy(2,4-di-tert-amylphenyl) benzoate (50 mg)
poly(N-tert-butylacrylamide) (300 mg)
N,N-diethyl-2,4-di-tert-amylphenoxyacetamide (100 mg)
2,5-di-tert-octylhydroquinone (50 mg)
red-sensitive silver chlorobromide emulsion (200 mg)
The top-most layer is prepared with and without a UV absorber:
with a UV absorber
2,5-di-tert-octylhydroquinone (20 mg)
hexyl 5-[2,5-dihydroxy-4-(4-hexyloxycarbpnyl-1,1-dimethylbutyl)phenyl]-5-methyl-hexanoate (20 mg)
gelatin (400 mg)
trinonyl phosphate (120 mg)
UV absorber test compound (385 mg)
without a UV absorber
gelatin (800 mg)

The hardener used is 2,4-dichloro-6-hydroxy-s-triazine potassium salt. The wetting agemt is the sodium salt of diisobutylhaphthalenesulfonic acid.

Three step wedges with a density difference of 0.3 log E per step are exposed onto each of the samples (with blue, green and red light, respectively). The processing process RA-4 (Kodak) for color papers is then carried out.

After exposure and processing, the reflectance densities in the red for the cyan step, in the green for the magenta step and in the blue for the yellow step are measured at a density of between 0.9 and 1.1 of the wedges. The wedges are then exposed in an Atlas exposure instrument at a total of 15 KJ/cm$^2$, and the reflectance densities are measured again.

In the case of the magenta wedge as well, the reflectance density before and after exposure is measured in the blue for yellowing.

The presence of the instant UV absorbers reduces the dye density loss of the cyan, magenta and yellow image dyes.

EXAMPLE 43

Photographic Compositions

The procedure described in Example 39 is repeated using a mixture of 1 part by weight of an instant UV absorber and 1 part by weight of a second instant UV absorber. Clear transparent coats are obtained which are suitable for a photographic recording material.

EXAMPLE 44

Photographic Compositions

The procedure described in Example 39 is repeated using a mixture of 1 part by weight of an instant UV absorber and 1 part by weight of a second benzotriazole UV absorber. Clear transparent coats are obtained which are suitable for a photographic recording material.

EXAMPLE 45

Automotive Coating Compositions

To ascertain the effect on thermal durability and loss rate from a high solids thermoset acrylic coating containing an instant benzotriazole UV absorber, the following tests are carried out.

A high solids thermoset acrylic clear coat is prepared by mixing an experimental acrylic polyol resin and hexamethoxymethylmelamine (Resimene® 747, Monsanto) at a solids ratio of 60/40. The dodecylbenzene sulfonic acid catalyst (Nacure® 5225; King Industries) is added at 0.70% by weight. A flow aid Modaflow® (Monsanto) is added at 0.25% by weight to form a model acrylic melamine resin system.

The model clear coat is reduced with xylene to a viscosity of 26–27 second using a Zahn #2 cup and applied via a conventional air spray at 50 psi (3.5 Kg/cm$^2$) over a 1"×3" (2.54 cm×7.62 cm) quartz slide. Cure is achieved by baking the slide for 30 minutes at 260° F. (127° C.). The clear coat is stabilized with 1% by weight of a hindered amine light stabilizer, bis-(1-octyloxy-2,2,6,6-tetramethylpiperidin-4-yl) sebacate, (TINUVIN® 123, Ciba). The various test benzotriazole UV absorbers are incorporated at the 5 mmol % by weight in the clear coat. The film thickness on the quartz slides range from 1.15 to 1.41 mils (0.029 to 0.036 mm).

The films on the quartz slides are weathered according to the following conditions in Xenon Arc Weather-Ometer with a controlled irradiance at 6500 W, using inner quartz and outer borosilicate S-type filter. The irradiation cycle is as follows: 40 minutes of straight irradiation with no water spray, followed by 20 minutes of light plus front spray, followed by 60 minutes of light irradiation and finally by 60 minutes dart plus rear spray (condensation). The setting is at 0.55 W/M$^2$ at 340 nm, 1.98 kJ/hour. In the light cycle the black panel temperature is controlled at 70±2° C. The relative humidity in the light cycle is in the range of 50–55% and in the dark cycle 100%. The absorbance of the long wavelength UV band as a function of Xenon arc weathering hours are recorded.

To follow the loss of UV absorbers from the clear coats, UV spectra are measured initially and after weathering at regular time intervals. The UV spectrophotometer measures absorbance linearly up to 5.5 absorbance units using a reference beam attenuation technique.

It is assumed that the degradation products from the UV absorber do not contribute to the UV spectrum. This is tested by following the ratio of absorbance of the band at about 300 nm and the band at about 340 nm. The ratio does not change upon weathering the sample. This suggests that the UV spectrum of the weathered films correspond to the amount of UV absorber remaining in the film with very little if any contribution to the spectrum by photo degradants.

Representative benzotriazole test compounds are incorporated into a high solid thermoset acrylic melamine resin at a concentration of 3% by weight to give equal molar concentrations of the test benzotriazole in equal film thickness and sufficient to give a starting absorbance of approximately 2.0 absorbance units. The test samples are exposed for 1026, 2025 and 3335 hours respectively.

| Compound of Example* | Units of Absorbance Loss after 1026 hours |
| --- | --- |
| TINUVIN ® 384* | 0.42 |
| Example 22 | 0.41 |
| Example 25 | 0.18 |
| Example 19 | 0.16 |
| Example 16 | 0.13 |

*TINUVIN ® 384 is 2-{2-hydroxy-3-tert-butyl-5-[2-(octyloxycarbonyl)ethyl]phenyl}-2H-benzotriazole.

| Compound of Example* | Units of Absorbance Loss after 2025 hours |
| --- | --- |
| TINUVIN ® 928* | 0.43 |
| Example 25 | 0.34 |
| Example 16 | 0.20 |

*TINUVIN ® 928 is 2-(2-hydroxy-3-α-cumyl-5-tert-octylphenyl)-2H-benzotriazole.

| Compound of Example* | Units of Absorbance Loss after 3336 hours |
| --- | --- |
| TINUVIN ® 928* | 0.69 |
| Example 25 | 0.60 |
| Example 16 | 0.30 |

*TINUVIN ® 928 is 2-(2-hydroxy-3-α-cumyl-5-tert-octylphenyl)-2H-benzotriazole.

The test shows that the instant benzotriazoles are especially durable in automotive coatings as judged by low loss rates.

EXAMPLE 46

Methyl 3-(Benzotriazol-2-yl)-4-hydroxy-5-(4-methoxy-α-cumyl)hydrocinnamate

Following the general procedure of Example 16, the title compound is prepared.

EXAMPLE 47

Methyl 3-(5-Chloro-benzotriazol-2-yl)-4-hydroxy-5-(4-chloro-α-cumyl)hydrocinnamate Following the general procedure of Example 16, the title compound is prepared.

EXAMPLE 48

Octyl 3-(5-Chloro-benzotriazol-2-yl)-4-hydroxy-5-(4-chloro-α-cumyl)hydrocinnamate The compound prepared in Example 47 is refluxed in toluene in the presence of lithium amide and EXXAL® 8 (mixture of octanols, Exxon-Mobil) for four hours. The title compound is obtained.

EXAMPLE 49

ω-Hydroxy-hepta-(ethyleneoxy)ethyl 3-(Benzotriazol-2-yl)-4-hydroxy-5-(4-methoxy-α-cumyl)hydrocinnamate and 3,6,9,12,15,18,21-Heptaoxatricosanylene Bis(3-(benzotriazol-2-yl)-4-hydroxy-5-(4-methoxy-α-cumyl)hydrocinnamate)

The methyl ester compound prepared in Example 46 is heated to 170° C. in the presence of poly(ethylene glycol) (molecular weight=300, available from DOW) and dibutyltin oxide, under a full vacuum, for four hours. The desired product which is a mixture of monomeric and dimeric esters depending on the stoichiometry is obtained.

EXAMPLE 50

Methyl 3-(5-Trifluoromethyl-benzotriazol-2-yl)-4-hydroxy-5-(2-fluoro-α-cumyl)hydrocinnamate Following the general procedure of Example 16, the title compound is prepared.

EXAMPLE 51

3-(5-Trifluoromethyl-benzotriazol-2-yl)-4-hydroxy-5-(2-fluoro-α-cumyl)hydrocinnamic Acid The title compound is prepared by refluxing the compound prepared in Example 50 in aqueous sodium hydroxide solution followed by neutralization with aqueous hydrochloric acid.

EXAMPLE 52

3-Methacryloyloxy-2-hydroxypropyl 3-(5-Trifluoromethyl-benzotriazol-2-yl)-4-hydroxy-5-(2-fluoro-α-cumyl)hydrocinnamate and 3-Methacryloyloxy-1-hydroxyprop-2-yl 3-(5-Trifluoromethyl-benzotriazol-2-yl)-4-hydroxy-5-(2-fluoro-α-cumyl)hydrocinnamate The desired mixture of the title compounds is obtained when the instant compound of Example 51, toluene, tetrabutylammonium bromide and glycidyl methacrylate are heated to 105° C. and held there for four hours. After cooling the reaction mixture to 80° C., washing thrice with water, the toluene is removed by vacuum distillation to give the desired mixture of title compounds.

EXAMPLES 53–71

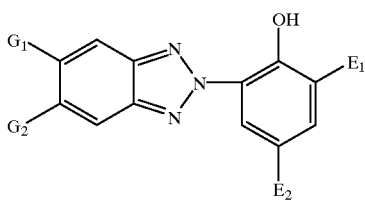

(I)

Following the general procedure of Example 16, the title compounds are prepared as represented by formula I (above) where $G_1$ and $G_2$ are hydrogen, $E_2$ is tert-butyl and $E_1$ is of formula IV:

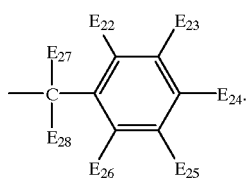

(IV)

$E_{25}$ is hydrogen in all examples.

| Example | $E_{27}$ | $E_{28}$ | $E_{22}$ | $E_{23}$ | $E_{24}$ | $E_{26}$ | $E_3$ or $G_3$ |
|---|---|---|---|---|---|---|---|
| 53 | Me | Me | Cl | H | Cl | Cl | — |
| 54 | Me | Me | Me | H | F | Me | — |
| 55 | Me | Me | H | IP | H | H | — |
| 56 | Me | Me | H | H | OAl | H | — |
| 57 | Oc | Oc | H | H | $CF_3$ | H | — |
| 58 | Me | Me | H | CN | H | H | — |
| 59 | Me | Me | H | H | OH | H | — |
| 60 | Do | H | OMe | H | OMe | OMe | — |
| 61 | Me | Me | H | H | * | H | — |
| 62 | Me | Me | H | H | ** | H | methyl |
| 63 | Et | Et | H | H | ** | H | allyl |
| 64 | Me | Me | H | ** | H | H | octadecyl |
| 65 | Me | Me | H | F | H | H | — |
| 66 | Me | Cy | H | H | *** | H | $E_{29}$ = Octa |
| 67 | Me | Me | H | H | **** | H | phenyl |
| 68 | Me | Me | H | H | **** | H | butyl |
| 69 | Me | Me | H | H | **** | H | dodecyl |
| 70 | Me | Me | H | H | $CF_3$ | H | — |
| 71 | Me | Me | H | H | $NHE_4$ | H | $E_4$ = Do |

In Examle 61, * is —$OCOE_{11}$ where $E_{11}$ is butyl.
 is —$COOG_3$; * is —$SO_2NHE_{29}$; **** is —$SO_2E_3$.
Do is dodecyl; Et is ethyl; IP is isopropenyl; Me is methyl; OAl is allyloxy; Oc is octyl; Octa is octadecyl; and OMe is methoxy.

EXAMPLE 72–90

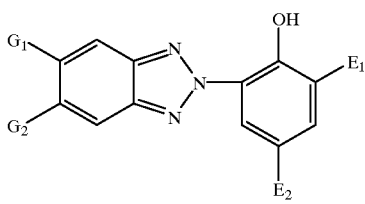

(I)

Following the general procedure of Example 16, the title compounds are prepared as represented by formula I (above) where $E_1$ is 4-chloro-α-cumyl in all examples.

| Example | $G_1$ | $G_2$ | $E_2$ | $G_3$ or $E_3$ | $E_6$ or $E_8$ |
|---|---|---|---|---|---|
| 72 | Cl | Cl | t-butyl | — | — |
| 73 | F | F | octyl | — | — |
| 74 | H | F | t-butyl | — | — |
| 75 | H | F | $EtCOOE_6$ | — | methyl |
| 76 | H | F | $EtCONHE_8$ | — | octadecyl |
| 77 | H | * | dodecyl | — | — |
| 78 | H | ** | octadecyl | ethyl | — |
| 79 | H | *** | t-butyl | methyl | — |
| 80 | H | *** | t-butyl | octyl | — |
| 81 | H | **** | octyl | octadecyl | — |
| 82 | H | $E_3SO$ | t-butyl | phenyl | — |
| 83 | H | $E_3SO_2$ | methyl | butyl | — |
| 84 | H | $E_3SO_2$ | methyl | octadecyl | — |
| 85 | H | $CF_3$ | t-octyl | — | — |
| 86 | H | $CF_3$ | EtOH | — | — |
| 87 | H | $CF_3$ | EtOAl | — | — |
| 88 | H | $CF_3$ | $EtCOOE_6$ | — | octyl |
| 89 | H | $CF_3$ | $EtCOOE_6$ | — | methyl |
| 90 | H | $CF_3$ | $EtCONHE_8$ | — | octadecyl |

$EtCOOE_6$ is $CH_2CH_2COOE_6$; $EtCONHE_8$ is $CH_2CH_2CONHE_8$; * is $P(O)(C_6H_5)_2$;  is $P(O)(OG_3)_2$; * is $COOG_3$; **** is $CONHG_3$; EtOH is $CH_2CH_2OH$; EtOAl is $CH_2CH_2OCH_2CH=CH_2$.

EXAMPLE 91

5-Carboxy-2-(2-hydroxy-3-(4-chloro-α-cumyl)-5-tert-butylphenyl)-2H-benzotriazole Following the general procedure of Example 16, the title compound is prepared. The structure is confirmed by [1]Hnmr and mass spectroscopic analyses. The title compound has a melting point of 287–288° C.

EXAMPLE 92

5-Methoxycarbonyl-2-(2-hydroxy-3-(4-chloro-α-cumyl)-5-tert-butylphenyl)-2H-benzotriazole The compound prepared in Example 91 (6.0 g, 0.012 mol), toluene (15 g, 0.16 mol), methanol (100 g, 3.1 mol) and concentrated sulfuric acid (0.4 g, 0.004 mol) are added to a reaction flask and heated to reflux. After eight hours at reflux, the solvents are removed by distillation and the residue is dissolved in 200 g of toluene. The solution is then passed through an absorbent (silica gel) to remove residual acid. The toluene is distilled off and the residue is twice recrystallized from methanol. The title compound is obtained in a yield of 4.9 g as a light yellow powder melting at 93–104° C. whose structure is consistent with [1]Hnmr and mass spectrometric analyses.

EXAMPLE 93

Poly(methyl methacrylate)

Poly(methyl methacrylate), medium molecular weight, Aldrich, is dissolved in methylene chloride at room temperature along with between 1 and 3% by weight of test benzotriazole, based on the PMMA resin. Films are cast using a calibrated drawdown bar to prepare 1 mil thick film after drying. The free standing films are mounted on cardboard holders, secured in metal frames and exposed in an Atlas C165 Xenon-arc Weather-Ometer under dry conditions according to ASTM G26. Performance is measured by a change in color or the physical integrity of the film, or in loss of absorbance of the UV absorber at λmax. Color measurements are carried out in an ACS spectrophotometer, small area view, spectral component included d/8, D65, 10° observer, YI 1925 for unexposed and exposed samples after 750 hours exposure.

| Compound of Example* (% by weight) | ΔYI |
|---|---|
| TINUVIN ® 234 (2.50%) | 1.34 |
| Example 25 (2.54%) | 0.75 |
| Example 28 (3.07%) | 0.93 |
| Example 31 (3.03%) | 0.81 |
| Example 32 (2.72%) | 0.46 |

*TINUVIN ® 234 is 2-(2-hydroxy-3,5-di-α-cumylphenyl)-2H-benzotriazole.

These data show that the instant compounds are particularly efficacious when used in thermoplastic compositions, such as poly(methyl methacrylate), even surpassing a commerical UV absorber in effectiveness. This is shown by the reduction of yellowing (ΔYI) after exposure to actinic radiation.

EXAMPLE 94

2-{2-Hydroxy-3-[4-(2-hydroxyethoxy)-α-cumyl]-5-tert-butylphenyl}-2H-benzotriazole When the compound of instant Example 59 is reacted with ethylene carbonate, the title compound is prepared.

EXAMPLE 95

2-{2-Hydroxy-3-[4-(2-bromoethoxy)-α-cumyl]-5-tert-butylphenyl}-2H-benzotriazole

When the compound of instant Example 94 is reacted with hydrobromic acid according to the procedure given in Brown & Patai, "The Chemistry of the Hydroxyl Group", Part 1, pages 595–622, the title compound is prepared.

EXAMPLE 96

2-{2-Hydroxy-3-[4-(2-phthalimidoethoxy)-α-cumyl]-5-tert-butylphenyl}-2H-benzotriazole When the compound of instant Example 95 is treated with potassium phthalimide according to Gibson & Bradshaw, Ange. Chem. Int. Ed. Engl., 7, 919–930 (1968), the title compound is prepared.

EXAMPLE 97

5-Trifluoromethyl-2-[2-hydroxy-3-(3-isopropenyl-α-cumyl)-5-tert-octylphenyl]-2H-benzotriazole The title compound is prepared following the general procedure given in instant Example 16.

EXAMPLE 98

5-Trifluoromethyl-2-{2-hydroxy-3-[3-(2-hydroxy-1-methylethyl)-α-cumyl]-5-tert-octylphenyl}-2H-benzotriazole;

When the compound of instant Example 97 is subjected to hydroboration conditions followed by alkaline hydrogen peroxide according to the procedure of J. March, "Advanced Organic Chemistry", 2nd Ed., McGraw-Hill, p. 720, the title compound is prepared.

EXAMPLE 99

5-Trifluoromethyl-2-{2-hydroxy-3-[3-(2-methacryloyloxy-1-methylethyl)-α-cumyl]-5-tert-octylphenyl}-2H-benzotriazole When the compound of instant Example 98 is refluxed in toluene with a molar equivalent of methacrylic acid and a catalytic amount of p-toluenesulfonic acid, the title compound is obtained.

EXAMPLE 100

5-Chloro-2-[2-hydroxy-3-(4-carboxy-α-cumyl)-5-methylphenyl]-2H-benzotriazole

Following the general procedure of instant Example 16, the title compound is prepared.

EXAMPLE 101

5-Chloro-2-[2-hydroxy-3-(4-octadecyloxycarbonyl-α-cumyl)-5-methylphenyl]-2H-benzotriazole When the compound of instant Example 100 is refluxed in toluene with a molar equivalent of octadecyl alcohol and a catalytic amount of p-toluenesulfonic acid, the title compound is obtained.

What is claimed is:

1. A compound of formula I, II or III

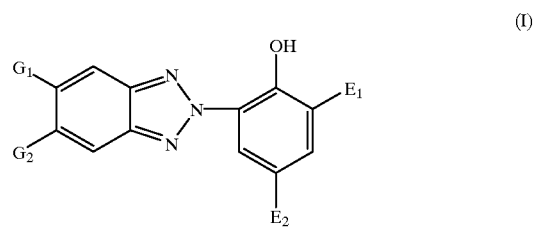
(I)

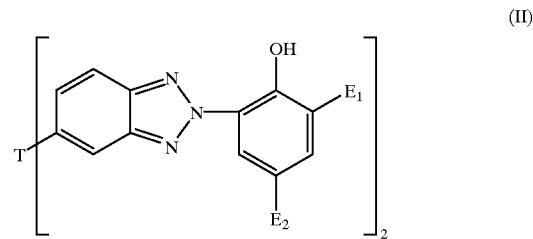
(II)

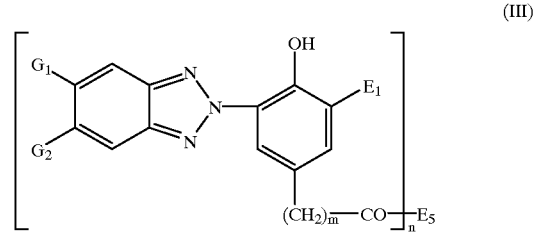
(III)

wherein $G_1$ is hydrogen or halogen, $G_2$ is hydrogen, cyano, perfluoroalkyl of 1 to 12 carbon atoms, halogen, —CO—$G_3$, —COO$G_3$, —CONH$G_3$, —CON($G_3$)$_2$, $E_3$SO—, $E_3$SO$_2$—, nitro, —P(O)(C$_6$H$_5$)$_2$, —P(O)(O$G_3$)$_2$,

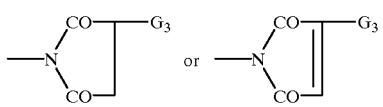

$G_3$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms, $E_1$ is hydrogen, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or $E_1$ is alkyl of 1 to 24 carbon atoms substituted by one or two hydroxy groups;

or $E_1$ is alkyl of 1 to 24 carbon atoms, alkenyl of 2 to 18 carbon atoms, said alkyl or said alkenyl substituted by one or more —$OCOE_{11}$, —$OE_4$, —NCO, —$NHCOE_{11}$, or —$NE_7E_8$, or mixtures thereof, where $E_4$ is straight or branched chain alkyl of 1 to 24 carbon atoms or straight or branched chain alkenyl of 2 to 18 carbon atoms; or said alkyl or said alkenyl interrupted by one or more —O—, —NH— or —$NE_4$— groups or mixtures thereof and which can be unsubstituted or substituted by one or more —OH, —$OE_4$ or —$NH_2$, or mixtures thereof;

or $E_1$ is a group of formula IV or V

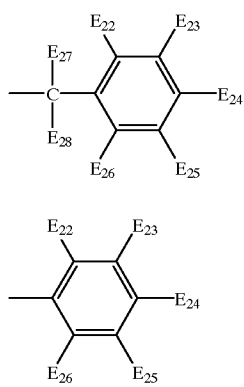

where
$E_{27}$ and $E_{28}$ are independently alkyl of 1 to 18 carbon atoms, or cycloalkyl of 5 to 12 carbon atoms;

$E_{22}$, $E_{23}$, $E_{24}$, $E_{25}$ and $E_{26}$ are independently hydrogen, halogen, straight or branched alkyl of 1 to 18 carbon atoms, alkenyl of 2 to 18 carbon atoms, said alkyl or said alkenyl substituted by one or more halogen, —$OCOE_{11}$, —$OE_4$, —NCO, —$NHCOE_{11}$, or —$NE_7E_8$, or mixtures thereof, where $E_4$ is straight or branched chain alkyl of 1 to 24 carbon atoms or straight or branched chain alkenyl of 2 to 18 carbon atoms; or said alkyl or said alkenyl interrupted by one or more —O—, —NH— or —$NE_4$— groups or mixtures thereof and which can be unsubstituted or substituted by one or more —OH, —$OE_4$ or —$NH_2$, or mixtures thereof; or $E_{22}$, $E_{23}$, $E_{24}$, $E_{25}$ and $E_{26}$ are independently phenyl, —OH, —$OCOE_{11}$, —$OE_{29}$, —NCO, —$NHCOE_{11}$ or —$NE_7E_8$, cyano, nitro, perfluoroalkyl of 1 to 12 carbon atoms, —$COG_3$, —$COOG_3$, —$CON(G_3)_2$, —$CONHG_3$, $E_3S$—, $E_3SO$—, $E_3SO_2$—, —P(O)($C_6H_5$)$_2$, —P(O))$OG_3$)$_2$, —$SO_2$—$X_1$—$E_{29}$;

$X_1$ is —O—, —NH— or —$NE_4$—;

$E_{29}$ is straight or branched chain alkyl of 1 to 24 carbon atoms, straight or branched chain alkenyl of 2 to 18 carbon atoms, said alkyl or said alkenyl substituted by one or more —OH, —$OCOE_{11}$, —$OE_4$, —NCO, —$NHCOE_{11}$, —$NE_7E_8$, phthalimido,

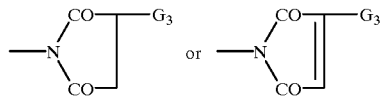

or mixtures thereof, where $E_4$ is straight or branched chain alkyl of 1 to 24 carbon atoms or alkenyl of 2 to 18 carbon atoms; or said alkyl or said alkenyl interrupted by one or more —O—, —NH— or —$NE_4$— groups or mixtures thereof and which can be unsubstituted or substituted by one or more —OH, —$OE_4$ or —$NH_2$, or mixtures thereof; or $E_{29}$ is phenyl or phenylalkyl of 7 to 15 carbon atoms, or said phenyl or said phenylalkyl substituted by one to three alkyl groups of 1 to 4 carbon atoms;

$E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ is alkyl of 1 to 24 carbon atoms or said alkenyl of 2 to 18 carbon atoms substituted by one or more —OH, —$OCOE_{11}$, —$OE_4$, —NCO, —$NHCOE_{11}$ or —$NE_7E_8$, or mixtures thereof, where $E_4$ is straight or branched chain alkyl of 1 to 24 carbon atoms or alkenyl of 2 to 18 carbon atoms; or said alkyl or said alkenyl interrupted by one or more —O—, —NH— or —$NE_4$— groups or mixtures thereof and which can be unsubstituted or substituted by one or more —OH, —$OE_4$ or —$NH_2$ groups or mixtures thereof, or $E_2$ is a group of formula IV or formula V as described above;

n is 1 or 2, when n is 1, $E_5$ is $OE_6$ or $NE_7E_8$, or $E_5$ is —PO($OE_{12}$)$_2$, —OSi($E_{11}$)$_3$ or —OCO—$E_{11}$, or straight or branched chain $C_1$–$C_{24}$alkyl which is interrupted by —O—, —S— or —$NE_{11}$ and which can be unsubstituted or substituted by —OH or —OCO—$E_{11}$, $C_5$–$C_{12}$ cycloalkyl which is unsubstituted or substituted by —OH, straight chain or branched $C_2$–$C_{18}$alkenyl which is unsubstituted or substituted by —OH, $C_7$–$C_{15}$aralkyl, —$CH_2$—CHOH—$E_{13}$ or glycidyl, $E_6$ is hydrogen, straight or branched chain $C_1$–$C_{24}$alkyl which is unsubstituted or substituted by one or more OH, $OE_4$ or $NH_2$ groups, or —$OE_6$ is —(OCH$_2$CH$_2$)$_w$OH or —(OCH$_2$CH$_2$)$_w$$OE_{21}$ where w is 1 to 12 and $E_{21}$ is alkyl of 1 to 12 carbon atoms, $E_7$ and $E_8$ are independently hydrogen, alkyl of 1 to 18 carbon atoms, straight or branched chain $C_3$–$C_{18}$alkyl which is interrupted by —O—, —S— or —$NE_{11}$—, straight or branched chain alkenyl of 2 to 18 carbon atoms, $C_5$–$C_{12}$cycloalkyl, $C_6$–$C_{14}$aryl or $C_1$–$C_3$hydroxylalkyl, or $E_7$ and $E_8$ together with the N atom are a pyrrolidine, piperidine, piperazine or morpholine ring, or $E_5$ is —X—(Z)$_p$—Y—$E_{15}$ wherein X is —O— or —N($E_{16}$)—, Y is —O— or —N($E_{17}$)—, Z is $C_2$–$C_{12}$-alkylene, $C_4$–$C_{12}$-alkylene interrupted by one to three nitrogen atoms, oxygen atoms or a mixture thereof, or is $C_3$–$C_{12}$-alkylene, butenylene, butynylene, cyclohexylene or phenylene, each substituted by a hydroxyl group, m is zero, 1 or 2, p is 1, or p is also zero when X and Y are —N($E_{16}$)— and —N($E_{17}$)—, respectively, $E_{15}$ is a group —CO—C($E_{18}$)=C(H)$E_{19}$ or, when Y is —N($E_{17}$)—, forms together with $E_{17}$ a group —CO—CH=CH—CO—, wherein $E_{18}$ is hydrogen or methyl, and $E_{19}$ is hydrogen, methyl or —CO—X—$E_{20}$, wherein $E_{20}$ is hydrogen, $C_1$–$C_{12}$-alkyl or a group of the formula:

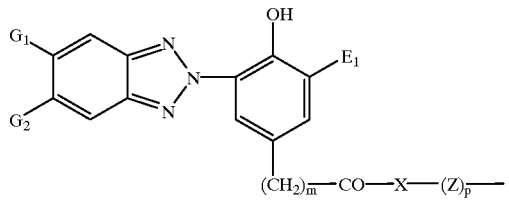

wherein the symbols $E_1$, $G_2$, X, Z, m and p have the meanings defined above, and $E_{16}$ and $E_{17}$ independently of one another are hydrogen, $C_1$–$C_{12}$-alkyl, $C_3$–$C_{12}$-alkyl interrupted by 1 to 3 oxygen atoms, or is cyclohexyl or $C_7$–$C_{15}$aralkyl, and $E_{16}$ together with $E_{17}$ in the case where Z is ethylene, also forms ethylene, when n is 2, $E_5$ is one of divalent radicals —O—$E_9$—O— or —N($E_{11}$)—$E_{10}$—N($E_{11}$)—, $E_9$ is $C_2$–$C_8$alkylene, $C_4$–$C_8$alkenylene, $C_4$alkynylene, cyclohexylene, straight or branched chain $C_4$–$C_{10}$alkylene which is interrupted by —O— or by —CH$_2$—CHOH—CH$_2$—O—$E_{14}$—O—CH$_2$—CHOH—CH$_2$—, $E_{10}$ being straight or branched chain $C_2$–$C_{12}$alkylene which may be interrupted by —O—, cyclohexylene, or

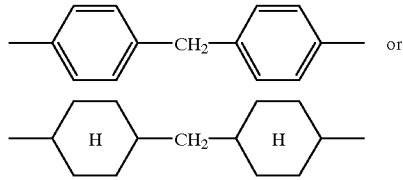

$E_{10}$ and $E_{11}$ with the two nitrogen atoms form a piperazine ring, $E_{14}$ is straight or branched chain $C_2$–$C_8$alkylene, straight or branched chain $C_4$–$C_{10}$alkylene which is interrupted by —O—, cycloalkylene, arylene or

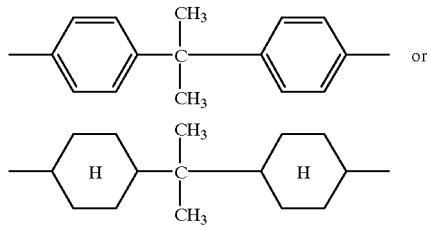

$E_{11}$ is hydrogen, straight or branched chain $C_1$–$C_{18}$alkyl, $C_5$–$C_{12}$cycloalkyl, straight or branched chain $C_2$–$C_{18}$alkenyl, $C_6$–$C_{14}$ aryl or $C_7$–$C_{15}$aralkyl, $E_{12}$ is straight or branched chain $C_1$–$C_{18}$alkyl, straight or branched chain $C_3$–$C_{18}$alkenyl, $C_5$–$C_{10}$cycloalkyl, $C_6$–$C_{16}$aryl or $C_7$–$C_{15}$aralkyl, $E_{13}$ is hydrogen, straight chain or branched $C_1$–$C_{18}$alkyl which is substituted by —PO(O$E_{12}$)$_2$, phenyl which is unsubstituted or substituted by OH, $C_7$–$C_{15}$aralkyl or —CH$_2$O$E_{12}$, $E_{13}$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, T is —SO—, —SO$_2$—, —SO—E—SO—, —SO$_2$—E—SO$_2$—, —CO—, —CO—CO—, —CO—CH$_2$—CO—, —CO—E—CO—, —COO—E—OCO— or —CO—NG$_5$—E—NG$_5$—CO—, where E is alkylene of 2 to 12 carbon atoms, cycloalkylene of 5 to 12 carbon atoms, or alkylene interrupted or terminated by cyclohexylene of 8 to 12 carbon atoms;

$G_5$ is $G_3$ or hydrogen, and with the proviso that at least one of $E_1$ and $E_2$ must contain a group of formula IV where $E_{22}$ to $E_{26}$ are not each hydrogen; where if 1 to 4 of $E_{22}$ to $E_{26}$ hydrogen, the remaining $E_{22}$ to $E_{26}$ groups are not each alkyl of 1 to 4 carbon atoms; and where if 4 of $E_{22}$ to $E_{26}$ are each hydrogen, the remaining $E_{22}$ to $E_{26}$ group is not halogen.

2. A compound of formula I according to claim 1:

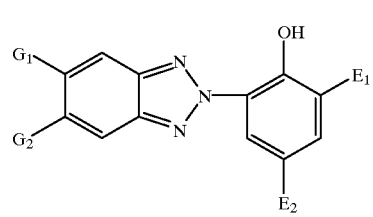

(I)

wherein $G_1$ is hydrogen, $G_2$ is hydrogen, cyano, CF$_3$—, fluoro, chloro, —CO—$G_3$, —COO$G_3$ or $E_3$SO$_2$—, $G_3$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms, $E_1$ is a group of formula IV or formula V wherein $E_{22}$–$E_{26}$ are independently hydrogen, alkyl of 1 to 12 carbon atoms, straight or branched chain alkenyl of 2 to 18 carbon atoms, OH, cyano, —O$E_{29}$, chloro, fluoro, —OCO$E_{11}$, CF$_3$, —COO$G_3$, $E_3$S—, $E_3$SO$_2$— or —SO$_2$—NH—$E_{29}$;

$E_{27}$ and $E_{28}$ are methyl;

$E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or $E_2$ is said alkyl of 1 to 24 carbon atoms or straight or branched alkenyl of 2 to 18 carbon atoms; or said alkyl or said alkenyl substituted by one or more —OH, —OCO$E_{11}$, —O$E_4$, —NCO, —NHCO$E_{11}$ or —N$E_7E_8$, or mixtures thereof, where $E_4$ is straight or branched chain alkyl of 1 to 24 carbon atoms or straight or branched chain alkenyl of 2 to 18 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$ groups or mixtures thereof; or $E_2$ is a group of formula IV or formula V wherein $E_{22}$–$E_{26}$ are independently hydrogen, alkyl of 1 to 12 carbon atoms, straight or branched chain alkenyl of 2 to 18 carbon atoms, OH, cyano, —OE$_{29}$, chloro, fluoro, —OCOE$_{11}$, CF$_3$, —COOG$_3$, E$_3$S—, E$_3$SO$_2$— or —SO$_2$—NH—E$_{29}$;

$E_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms; and where $E_{11}$ and $E_{29}$ are as defined above.

3. A compound of formula I according to claim 1 which is
a. 5-trifluoromethyl-2-[2-hydroxy-3-(4-methoxy-α-cumyl)-5-tert-butylphenyl]-2H-benzotriazole;
b. 5-trifluoromethyl-2-[2-hydroxy-3-(4-fluoro-α-cumyl)-5-tert-octylphenyl]-2H-benzotriazole;
c. 2-[2-hydroxy-3-(4-methoxy-α-cumyl)-5-tert-butylphenyl]-2H-benzotriazole;
d. 2-[2-hydroxy-3-(4-chloro-α-cumyl)-5-tert-butylphenyl]-2H-benzotriazole;
e. 5-chloro-2-[2-hydroxy-3-(4-chloro-α-cumyl)-5-tert-butylphenyl]-2H-benzotriazole;
f. 5-chloro-2-[2-hydroxy-3,5-di-(4-chloro-α-cumyl) phenyl]-2H-benzotriazole;
g. 5-chloro-2-[2-hydroxy-3,5-di-(4-methoxy-α-cumyl) phenyl]-2H-benzotriazole;
h. 5-trifluoromethyl-2-[2-hydroxy-3-(4-chloro-α-cumyl)-5-tert-butylphenyl]-2H-benzotriazole;
i. 5-chloro-2-[2-hydroxy-3-(4-methoxy-α-cumyl)-5-tert-butylphenyl]-2H-benzotriazole;
j. 2-{2-hydroxy-3-[4-(2-dimethylaminoethyl)aminosulfonyl-α-cumyl]-5-tert-octylphenyl}-2H-benzotriazole;
k. 2-{2-hydroxy-3-[4-(3-dimethylaminopropyl)aminosulfonyl-α-cumyl]-5-tert-octylphenyl}-2H-benzotriazole;
l. 5-carboxy-2-[2-hydroxy-3-(4-chloro-α-cumyl)-5-tert-butylphenyl]-2H-benzotriazole;
m. 5-methoxycarbonyl-2-[2-hydroxy-3-(4-chloro-α-cumyl)-5-tert-butylphenyl]-2H-benzotriazole;
n. 2-{2-hydroxy-3-[4-(2-hydroxyethoxy)-α-cumyl]-5-tert-butylphenyl}-2H-benzotriazole;
o. 2-{2-hydroxy-3-[4-(2-phthalimidoethoxy)-α-cumyl]-5-tert-butylphenyl}-2H-benzotriazole;
p. 5-trifluoromethyl-2-[2-hydroxy-3-(3-isopropenyl-α-cumyl)-5-tert-octylphenyl]-2H-benzotriazole;
q. 5-trifluoromethyl-2-{2-hydroxy-3-[3-(2-hydroxy-1-methylethyl)-α-cumyl]-5-tert-octylphenyl)-2H-benzotriazole;
r. 5-trifluoromethyl-2-{2-hydroxy-3-[3-(2-methacryloyloxy-1-methylethyl)-α-cumyl]-5-tert-octylphenyl}-2H-benzotriazole;
s. 5-chloro-2-[2-hydroxy-3-(4-carboxy-α-cumyl)-5-methylphenyl]-2H-benzotriazole;
t. 5-chloro-2-[2-hydroxy-3-(4-octadecyloxycarbonyl-α-cumyl)-5-methylphenyl]-2H-benzotriazole; or
u. 2-[2-hydroxy-3-(4-octadecylaminosulfonyl-α-cumyl)-5-tert-octylphenyl]-2H-benzotriazole.

4. A stabilized composition which comprises
(a) an organic material subject to degradation by heat, light or oxygen, and
(b) an effective stabilizing amount of a compound of formula I, II or III according to claim 1.

5. A composition according to claim 4 wherein component (a) is a thermoplastic polyolefin, polyester, polyester urethane, polyether urethane or a water-borne coating.

6. A composition according to claim 5 wherein component (a) is selected from the group consisting of polypropylene, thermoplastic polyolefin, low density polyethylene, medium density polyethylene, high density polyethylene, linear low density polyethylene, poly(butene-1), ethylene/vinyl acetate copolymer, ethylene/propylene copolymer, copolymers of ethylene or propylene with other alpha-olefins, copolymers of acrylonitrile-butadiene-styrene (ABS), copolymers of acrylonitrile and styrene that are impact modified with ethylene-propylene rubber or ethylene/propylene/alpha-olefin rubber or butyl acrylate rubber, blends of ABS and polycarbonate, blends of ABS and poly(vinyl chloride) (PVC), poly(vinyl chloride), copolymers of styrene and butadiene (HIPS), copolymers of styrene and butadiene that also contain ethylene-propylene rubber or ethylene/propylene/alpha-olefin rubber or butyl acrylate rubber, thermoplastic elastomers and thermoplastic vulcanizates.

7. A composition according to claim 5 wherein component (a) is a polyester or polyether urethane or water-borne coating.

8. A composition according to claim 6 which additionally contains an effective stabilizing amount of at least one coadditive stabilizer selected from the group consisting of the phenolic antioxidants, metal stearates, metal oxides, organophosphorus compounds, furanone antioxidants, hydroxylamines, UV absorbers, non-NOR hindered amines, NOR hindered amines and mixtures thereof.

9. A composition according to claim 6 which additionally contains a filler.

10. A composition according to claim 9 wherein the filler is calcium carbonate, clay, talc, mica or glass.

11. A composition according to claim 6 wherein component (a) is a polyolefin film, fiber or thick section, ABS, high impact polystyrene (HIPS), thermoplastic polyolefin, thermoplastic elastomer or thermoplastic vulcanizate which additionally contains a halogenated flame retardant.

12. A composition according to claim 11 wherein the flame retardant is tris[3-bromo-2,2-bis(bromomethyl)propyl]phosphate, decabromodiphenyl oxide, ethylene bis(tetrabromophthalimide) or ethylene bis(dibromonorbornanedicarboximide).

13. A composition according to claim 6 wherein component (a) is polypropylene fiber.

14. A composition according to claim 6 wherein component (a) is polypropylene, polyethylene or thermoplastic polyolefin (TPO).

15. A composition according to claim 14 wherein component (a) is a paintable thermoplastic olefin (TPO).

16. A composition according to claim 4 which additionally comprises a coadditive stabilizer which is a hindered phenolic antioxidant selected from the group consisting of neopentanetetrayl tetrakis(3,5-di-tert-butyl-4-hydroxyhydrocinnamate, octadecyl 3,5-di-tert-butyl-4-hydroxyhydrocinnamate, 1,3,5-trimethyl-2,4,6-tris(3,5,-di-tert-butyl-4-hydroxybenzyl)benzene, 1,2-bis(3,5-di-tert-butyl-4-hydroxyhydrocinnamoyl)hydrazine, calcium [bis (monoethyl 3,5-ditert-butyl-4-hydroxybenzyl) phosphonate], 1,3,5-tris(3,5 -di-tert-butyl-4-hydroxybenzyl) isocyanurate and 1,3,5-tris(3-hydroxy-4-tert-butyl-2,6-dimethylbenzyl)isocyanurate; or is an organophosphorus stabilizer selected from the group consisting of tris(2,4-di-tert-butylphenyl)phosphite, bis(2,4-di-tert-butyl-6-methylphenyl)ethyl phosphite, 2,2',2"-nitrile[triethyl-tris-(3,3',5,5'-tetra-tert-butyl-1,1'-biphenyl-2,2'-diyl)phosphite], tetrakis(2,4-di-butylphenyl) 4,4'-biphenylenediphosphonite, tris(nonylphenyl)phosphite, bis(2,4-di-tert-butylphenyl) pentaerythritol diphosphite, 2,2'-ethylidenebis(2,4-di-tert-butylphenyl)fluorophosphite and 2-butyl-2-ethylpropan-1,3-diyl 2,4,6-tri-tert-butylphenyl phosphite; or is 5,7-di-tert-butyl-3-(3,4-dimethylphenyl)-2H-benzofuran-2-one; or is N,N-dialkylhydroxylamine made by the direct oxidation of N,N-di(hydrogenated tallow)amine; or is a hindered amine selected from the group consisting of bis(2,2,6,6-tetramethylpiperidin-4-yl)sebacate, the polycondensation product of 1-(2-hydroxyethyl)-2,2,6,6-tetramethyl-4-hydroxypiperidine and succinic acid, N,N',N",N"'-tetrakis[4,6-bis(butyl-1,2,2,6,6-pentamethylpiperidin-4-yl)amino-s-triazin-2-yl]-1,10-diamino-4,7-diazadecane, the polycondensation product of 4,4'-hexamethylenebis(amino-2,2,6,6-tetramethylpiperidine) and 2,4-dichloro-6-tert-octylamino-s-triazine, the polycondensation product of 4,4'-hexamethylenebis(amino-2,2,6,6-tetramethylpiperidine) and 2,4-dichloro-6-morpholino-s-triazine, the polycondensation product of 4,4'-hexamethylenebis(amino-1,2,2,6,6-pentamethylpiperidine) and 2,4-dichloro-6-morpholino-s-triazine, 2,2,6,6-tetramethylpiperidin-4-yl octadecanoate, 3-dodecyl-1-(1-acetyl-2,2,6,6-tetramethylpiperidin-4-yl)pyrrolidin-2,5-dione, 1,3,5-tris{N-cyclohexyl-N-[2-(2,2,6,6-tetramethylpiperazin-3-on-4-yl)ethyl]amino}-s-triazine, poly[methyl 3-(2,2,6,6-tetramethylpiperidin-4-yloxy) propyl]siloxane, the polycondensation product of 2,4-dichloro-6-(2,2,6,6-tetramethylpiperidin-4-yl)butylamino)-s-triazine, 2,2'ethylene-bis{[2,4-(2,2,6,6-tetramethylpiperidin-4-yl)butylamino-s-triazin-6-yl] aminotrimethyleneamino}, oligomer of N-{[2-(N-2,2,6,6-tetramethylpiperidin-4-yl)butylamino]-s-triazin-4-yl}-N,N'-bis(2,2,6,6-tetramethylpiperidin-4-yl)-1,6-hexanediamine terminated with 2,4-bis(dibutylamino)-s-triazin-6-yl, N,N',N"-tris{2,4-bis[N-(1,2,2,6,6-pentamethylpiperidin-4-yl) butylamino]-s-triazin-6-yl}-3,3'-ethylenediiminodipropylamine, N,N',N"'-tris (2,4-bis[N-(1,2,2,6,6-pentamethylpiperidin-4-yl)butylamino]-s-triazin-6-yl}-3,3'-ethylenediiminodipropylamine and N,N',N",N"'-tetrakis{2,4-bis[N-(1,2,2,6,6-pentamethylpiperidin-4-yl) butylamino]-s-triazin-6-yl}-3,3' -ethylenediiminodipropylamine; or is another N-hydrocarbyloxy substituted hindered amines selected from the group consisting of bis(1-octyloxy-2,2,6,6-tetramethylpiperidin-4-yl)sebacate, bis(1-octyloxy-2,2,6,6-tetramethylpiperidin-4-yl)adipate, bis(1-cyclohexyloxy-2,2,6,6-tetramethylpiperidin-4-yl)adipate, bis(1-cyclohexyloxy-2,2,6,6-tetramethylpiperidin-4-yl)sebacate, 1-cyclohexyloxy-2,2,6,6-tetramethylpiperidin-4-yl octadecanoate, N,N',N"-tris{2,4-bis[N-(1-cyclohexyloxy-2,2,6,6-tetramethylpiperidin-4-yl)butylamino]-s-triazin-6-yl}-3,3'-ethylenediiminodipropylamine, N,N',N"'-tris{2,4-bis[N-(1-cyclohexyloxy-2,2,6,6-tetramethylpiperidin-4-yl) butylamino]-s-triazin-6-yl}-3,3'-ethylenediiminodipropylamine and N,N',N",N"'-tetrakis{2,4-bis[N-(1-cyclohexyloxy-2,2,6,6-tetramethylpiperidin-4-yl)butylamino]-s-triazin-6-yl}-3,3'-ethylenediiminodipropylamine; or a hydroxy substituted N-hydrocarbyloxy substituted hindered amine selected from the group consisting of bis[1-(2-hydroxy-2-methylpropoxy)-2,2,6,6-tetramethylpiperidin-4-yl)] sebacate; a mixture of bis[1-(2-hydroxy-2-methylpropoxy)-2,2,6,6-tetramethylpiperidin-4-yl]glutarate and bis[1-(2-hydroxy-2-methylpropoxy)-2,2,6,6-tetramethylpiperidin-4-yl]adipate; 1-(2-hydroxy-2-methylpropoxy)-4-octadecanoyloxy-2,2,6,6-tetramethylpiperidine; bis[1-(2-hydroxy-2-methylpropoxy)-2,2,6,6-tetramethylpiperidin-4-yl]adipate; bis[1-(2-hydroxy-2-methylpropoxy)-2,2,6,6-tetramethylpiperidin-4-yl]glutarate; bis[1-(2-hydroxy-2-methylpropoxy)-2,2,6,6-tetramethylpiperidin-4-yl] succinate; a mixture of bis[1-(2-hydroxy-2-methylpropoxy)-2,2,6,6-tetramethylpiperidin-4-yl]glutarate and bis[1-(2-hydroxy-2-methylpropoxy)-2,2,6,6-tetramethylpiperidin-4-yl]succinate; 1-(4-octadecanoyloxy-2,2,6,6-tetramethylpiperidin-1-yloxy)-2-octadecanoyloxy-2-methylpropane; 1-(2-hydroxy-2-methylpropoxy)-4-[9-(methoxy-carbonyl)nonanoyloxy]-2,2,6,6-tetramethylpiperidine; 1-(2-hydroxy-2-methylpropoxy)-4-[5-(methoxy-carbonyl)pentanoyloxy]-2,2,6,6-tetramethylpiperidine; 1-(2-hydroxy-2-methylpropoxy)-4-[3-(methoxy-carbonyl)propionyloxy]-2,2,6,6-tetramethylpiperidine; 1-(2-hydroxy-2-methylpropoxy)-4-[4-(methoxy-carbonyl)butyryloxy]-2,2,6,6-tetramethylpiperidine; or is a UV absorber selected from the group consisting of 2-(2-hydroxy-3,5-di-α-cumylphenyl)-2H-benzotriazole, 2-(2-hydroxy-5-methylphenyl)-2H-benzotriazole, 5-chloro-2-(2-hydroxy-3,5-di-tert-butylphenyl)-2H-benzotriazole, 2-(2-hydroxy-3,5-di-tert-amylphenyl)-2H-benzotriazole, 2-(2-hydroxy-3-α-cumyl-5-tert-octylphenyl)-2H-benzotriazole, 2,4-di-tert-butylphenyl 3,5-di-tert-butyl4-hydroxybenzoate, 2-hydroxy-4-n-octyloxybenzophenone, 2,4-bis(2,4-dimethylphenyl)-6-(2-hydroxy-4-octyloxyphenyl)-s-triazine, oligomer of N-{2-[(1-propoxy-2,2,6,6-tetramethylpiperidin-4-yl)butylamino]-s-triazin-4-yl}-N,N'-bis(1-propoxy-2,2,6,6-tetramethylpiperidin-4-yl)-1,6-hexanediamine terminated with 2,4-bis(dibutylamino)-s-triazin-6-yl, the condensation product of 2-morpholino-4,6-dichloro-s-triazine with N,N'-bis(1,2,2,6,6-pentamethylpiperidin-4-yl)-1,6-hexanediamine; or mixtures thereof.

17. A composition according to claim 16 wherein the coadditive stabilizer is neopentanetetrayl tetrakis(3,5-di-tert-butyl-4-hydroxyhydrocinnamate, tris(2,4-di-tert-butylphenyl)phosphite, N,N-dialkylhydroxylamine made by the direct oxidation of N,N-di(hydrogenated tallow)amine, N,N',N",N"'-tetrakis[4,6-bis(butyl-1,2,2,6,6-pentamethylpiperidin-4-yl)amino-s-triazin-2-yl]-1,10-diamino-4,7-diazadecane, the polycondensation product of 4,4'-hexamethylenebis(amino-2,2,6,6-tetramethylpiperidine) and 2,4-dichloro-6-tert-octylamino-s-triazine, the polycondensation product of 4,4'-hexamethylenebis(amino-2,2,6,6-tetramethylpiperidine) and 2,4-dichloro-6-morpholino-s-triazine, the polycondensation product of 4,4'-hexamethylenebis(amino-1,2,2,6,6-pentamethylpiperidine) and 2,4-dichloro-6-morpholino-s-triazine, oligomer of N-{[2-(N-2,2,6,6-tetramethylpiperidin-4-yl)butylamino]-s-triazin-4-yl}-N,N'-bis(2,2,6,6-tetramethylpiperidin-4-yl)-1,6-hexanediamine terminated with 2,4-bis(dibutylamino)-s-triazin-6-yl, N,N',N"-tris(2,4-bis[N-(1,2,2,6,6-pentamethylpiperidin-4-yl)butylamino]-s-triazin-6-yl}-3,3'-ethylenediiminodipropylamine, N,N',N"'-tris(2,4-bis[N-(1,2,2,6,6-pentamethylpiperidin-4-yl) butylamino]-s-triazin-6-yl}-3,3'-ethylenediiminodipropylamine and N,N',N",N"'-tetrakis{2,4-bis[N-(1,2,2,6,6-pentamethylpiperidin-4-yl)butylamino]-s-triazin-6-yl}-3,3'-ethylenediiminodipropylamine, oligomer of N-{2-[(1-propoxy-2,2,6,6-tetramethylpiperidin-4-yl)butylamino]-s-triazin-4-yl}-N,N'-bis(1-propoxy-2,2,6,6-tetramethylpiperidin-4-yl)-1,6-hexanediamine terminated with 2,4-bis(dibutylamino)-s-triazin-6-yl, or the condensation product of 2-morpholino-4,6-dichloro-s-triazine with N,N'-bis(1,2,2,6,6-pentamethylpiperidin-4-yl)-1,6-hexanediamine.

18. A composition according to claim 4 which additionally contains another UV absorber selected from the group consisting of the benzotriazoles, the s-triazines, the oxanilides, the salicylates, the hydroxybenzophenones, the benzoates and the α-cyanoacrylates.

19. A composition according to claim 4 which additionally contains a UV absorber selected from the group consisting of
(a) 5-trifluoromethyl-2-(2-hydroxy-3-α-cumyl-5-tert-octylphenyl)-2H-benzotriazole;
(b) 5-trifluoromethyl-2-(2-hydroxy-5-tert-octylphenyl)-2H-benzotriazole;
(c) 5-trifluoromethyl-2-(2-hydroxy-3,5-di-tert-octylphenyl)-2H-benzotriazole;
(d) 2,2'-methylene-bis[6-(5-trifluoromethyl-2H-benzotriazol-2-yl)-4-tert-octylphenol];
(e) methylene-2-[4-tert-octyl-6-(2H-benzotriazol-2-yl)phenol]2'-[4-tert-octyl-6-(5-trifluoromethyl-2H-benzotriazol-2-yl)phenol];
(f) 3-(5-trifluoromethyl-2H-benzotriazol-2-yl)-5-tert-butyl-4-hydroxyhydrocinnamic acid;
(g) methyl 3-(5-trifluoromethyl-2H-benzotriazol-2-yl)-5-tert-butyl-4-hydroxyhydrocinnamate;
(h) isooctyl 3-(5-trifluoromethyl-2H-benzotriazol-2-yl)-5-tert-butyl-4-hydroxyhydrocinnamate;
(i) 5-trifluoromethyl-2-[2-hydroxy-5-(3-hydroxypropyl)phenyl]-2H-benzotriazole;
(j) 5-trifluoromethyl-2-[2-hydroxy-5-(3-acryloyloxypropyl)phenyl]-2H-benzotriazole;
(k) 5-trifluoromethyl-2-[2-hydroxy-5-(3-methacryloyloxypropyl)phenyl]-2H-benzotriazole;
(l) 5-trifluoromethyl-2-[2-hydroxy-5-(3-acrylylaminopropyl)phenyl]-2H-benzotriazole;
(m) 5-trifluoromethyl-2-[2-hydroxy-5-(3-methacrylylaminopropyl)phenyl]-2H-benzotriazole;
(n) 5-trifluoromethyl-2-(2-hydroxy-3-α-cumyl-5-tert-butylphenyl)-2H-benzotriazole;
(o) 5-trifluoromethyl-2-(2-hydroxy-3-α-cumyl-5-nonylphenyl)-2H-benzotriazole;
(p) 5-trifluoromethyl-2-[2-hydroxy-3-α-cumyl-5-(2-hydroxyethyl)phenyl]-2H-benzotriazole;
(q) 5-trifluoromethyl-2-[2-hydroxy-3-α-cumyl-5-(3-hydroxypropyl)phenyl]-2H-benzotriazole;
(r) 5-trifluoromethyl-2-(2-hydroxy-3,5-di-tert-amylphenyl)-2H-benzotriazole;
(s) 5-trifluoromethyl-2-(2-hydroxy-3,5-di-tert-butylphenyl)-2H-benzotriazole;
(t) 5-trifluoromethyl-2-(2-hydroxy-3-dodecyl-5-methylphenyl)-2H-benzotriazole;
(u) 5-trifluoromethyl-2-[2-hydroxy-3-tert-butyl-5-(3-hydroxypropyl)phenyl)-2H-benzotriazole;
(v) 5-trifluoromethyl-2-[2-hydroxy-3-tert-butyl-5-(2-hydroxyethyl)phenyl]-2H-benzotriazole;
(w) 5-trifluoromethyl-2-[2-hydroxy-5-(2-hydroxyethyl)phenyl]-2H-benzotriazole;
(x) 5-trifluoromethyl-2-(2-hydroxy-3,5-di-α-cumylphenyl)-2H-benzotriazole;
(y) 5-fluoro-2-(2-hydroxy-3,5-di-α-cumylphenyl)-2H-benzotriazole;
(z) 5-butylsulfonyl-2-(2-hydroxy-3,5-di-α-cumylphenyl)-2H-benzotriazole;
(aa) 5-butylsulfonyl-2-(2-hydroxy-3,5-di-tert-butylphenyl)-2H-benzotriazole;
(bb) 5-butylsulfonyl-2-(2-hydroxy-3,5-di-tert-octylphenyl)-2H-benzotriazole; and
(cc) 5-phenylsulfonyl-2-(2-hydroxy-3,5-di-tert-butylphenyl)-2H-benzotriazole.

20. A composition according to claim 4 which is a stabilized stoving lacquer wherein component (a) is an acid catalyzed resin based on hot crosslinkable, acrylic, acrylic melamine, polyester, polyurethane, polyamide or alkyd resin.

21. A composition according to claim 20 which additionally contains another UV absorber selected from the group consisting of the benzotriazoles, the s-triazines, the oxanilides, the salicylates, the hydroxybenzophenones, the benzoates and the α-cyanoacrylates.

22. A composition according to claim 20 which is an enamel of high solids content for industrial finishes.

23. A composition according to claim 22 which is a finishing enamel for automobiles.

24. A composition according to claim 4 which is a stabilized ambient curable composition wherein component (a) is a resin selected from the group consisting of unmodified or modified alkyd resin, acrylic resin, acrylic alkyd resin, polyester resin or crosslinkable epoxide resin.

25. A composition according to claim 24 wherein the resin is selected from the group consisting of unmodified alkyl, acrylic, acrylic alkyd or polyester resins; said resins modified with silicon, isocyanates, isocyanurates, ketimines or oxazolidines; crosslinked epoxy resins; and epoxy-crosslinked acrylic and polyester resins.

26. A composition according to claim 25 which is an enamel of high solids content for industrial finishes.

27. A composition according to claim 26 which is a finishing enamel for automobiles.

28. A composition according to claim 27 which is a curable electrocoat composition wherein component (a) is an amino-group containing resin having functional groups that are reactive with an isocyanate and an aromatic polyisocyanate crosslinking agent.

29. A composition according to claim 4 which is a non-gelling liquid coating composition wherein component (a) comprises (A) at least one acrylic monomer, (B) silica and (C) at least one initiator for ultraviolet radication-induced curing of said composition.

30. A composition according to claim 29 which contains a silyl acrylate, a polyfunctional acrylate, silica and a photoinitiator.

31. A composition according to claim 4 wherein component (a) is a polyolefin, polycarbonate, a styrenic, ABS, a nylon (polyamide), a polyester, a polyurethane, a polyacrylate, a rubber modified styrenic, poly(vinyl chloride), poly(vinyl butyral), polyacetal (polyoxymethylene), or other blends or copolymers such as poly(ethylene/1,4-cyclohexylenedimethylene terephthalate) PETG or an ethylene/acrylic acid copolymer or salts thereof (an ionomer).

32. A composition according to claim 31 wherein the polymer is a polyester or a polyacrylate.

33. A composition according to claim 32 wherein the polyester is poly(ethylene terephthalate), poly(butylene terephthalate) or poly(ethylene naphthalenedicarboxylate), or copolymer poly(ethylene/1,4-cyclohexylenedimethylene terephthalate) PETG.

34. A composition according to claim 4 wherein component (a) is a thermoplastic polymer.

35. A composition according to claim 34 wherein the polymer is a polyolefin or polycarbonate.

36. A composition according to claim 35 wherein the polymer is polyethylene or polypropylene.

37. A composition according to claim 4 wherein component (a) is a photographic composition.

38. A composition according to claim 35 wherein the polymer is polycarbonate.

39. A composition according to claim 32 wherein the polymer is a polyacrylate.

40. A composition according to claim 39 wherein the polyacrylate is poly(methyl methacrylate).

* * * * *